United States Patent
Jia et al.

(10) Patent No.: US 12,037,608 B2
(45) Date of Patent: Jul. 16, 2024

(54) GENETICALLY ENGINEERED COXSACKIEVIRUS, AND PHARMACEUTICAL COMPOSITION

(71) Applicants: THE UNIVERSITY OF TOKYO, T

(56) References Cited

OTHER PUBLICATIONS

Lei, Wen et al., Combined expression of miR-34a and Smac mediated by oncolytic vaccinia virus synergistically promote anti-tumor effects in Multiple Myeloma, www.nature.com/scientificreports, Aug. 24, 2016, pp. 1-11.

* cited by examiner

FIG. 3 miR-34a: UGG CAG UGU CUU AGC UGG UUG U (miRBass ID: MIMAT0000255)

miR-34c: AGG CAG UGU AGU UAG CUG AUU GC (miRBass ID: MIMAT0000686)

5' Insert(743bp)  
Immediately upsteream of the start codon

3' Insert(7,305bp)

FIG. 6

5' UTR

742 tcattgttaagttgaatacagcaaaGCAATCAGCTAACTACACTGCCTcgatGCAATCAGCTA

ACTACACTGCCTaccggtGCAATCAGCTAACTACACTGCCTtcacGCAATCAGCTAACT

742

ACACTGCCTatgggagctcaagtatcaacgcaaaagactggggcacatgagaccAggctgaatgctagc
          Start codon ggcaattccatcattcactacacaaatatta Non-transfected

H1299

MOCK
MOI=$10^{-4}$
MOI=$10^{-3}$
MOI=$10^{-2}$
MOI=$10^{-1}$
MOI=1

① CVB3-WT

② CVB3-34a-3

③ CVB3-34a-5

④ CVB3-34a-53

⑤ CVB3-34a&217-53 miRNA-34a transfected H1299

BASE-2B

① CVB3-WT

② CVB3-miR-1&217T

③ CVB3-34a-3

④ CVB3-34c-3

FIG. 16

① CVB3-34a-3 (P3)

② CVB3-34c-3 (P3)

③ CVB3-34a-3 (P6)

④ CVB3-34c-3 (P6)

⑤ CVB3-34a-3 (P10)

⑥ CVB3-34c-3 (P10)

5' UTR

3' UTR

GENETICALLY ENGINEERED COXSACKIEVIRUS, AND PHARMACEUTICAL COMPOSITION

specifically in the pancreas and another is miR-1 that is said to be expressed specifically in muscle tissue and normal cells.

Also, in studying insertion of a target sequence for a specific miRNA into a genome, it was determined that even in the 3' UTR, virus replication is hindered depending on the insertion position, and a finding that an appropriate insertion position must be found was thereby obtained. An optimal position was thus determined for the position of insertion of the target sequence for the miRNA into the genome. Also, a position of insertion of a target sequence for a specific miRNA into the genome in the 5' UTR was studied to determine an insertion position of the target sequence with which gene replication is not hindered.

Further, a study was performed upon noting that by using the 5' UTR as the position of insertion of the target sequence for the specific miRNA into the genome, there is a possibility that detachment of the inserted target sequence from the virus genome becomes unlikely.

To achieve the above object, a gene-modified coxsackievirus of the present invention contains a mutated genome with a coxsackievirus wild-type (CVB3-WT) genome inserted with at least one polynucleotide constituted of a target sequence for a normal-cell-specific or tissue-specific microRNA (miRNA) and has an arrangement with which proliferation is suppressed specifically in normal cells and the target sequence for the normal-cell-specific miRNA corresponds to at least one of miR-34a and miR-34c.

Here, by containing the mutated genome with the coxsackievirus wild-type (CVB3-WT) genome inserted with at least one polynucleotide constituted of the target sequence for the normal-cell-specific or tissue-specific microRNA (miRNA), virus proliferation can be suppressed in tissue in which the miRNA is present. That is, a RISC complex that contains the miRNA binds to the inserted target sequence to inhibit virus protein translation and virus proliferation can thus be suppressed tissue-specifically.

Also, by the target sequence for the normal-cell-specific miRNA corresponding to at least one of miR-34a and miR-34c, virus proliferation can be suppressed in tissue in which miR-34a or miR-34c is present. That is, the miR-34 family that includes miR-34a and miR-34c is expressed highly in normal cells and therefore virus proliferation in normal cells can be suppressed to improve safety. Also, in tissue in which miR-34a or miR-34c is not present, that is, in cancer cells in which deletion or reduction of expression of the miR-34 family is seen, the virus can proliferate to enable antitumor effects to be exhibited selectively.

Also, if a position at which the polynucleotide is inserted is at least one of either of inside the 5' UTR region and inside the 3' UTR region of the CVB3-WT genome, replication is unlikely to be hindered during virus replication within host cells. That is, the 5' UTR region or the 3' UTR region is an untranslated region that is not translated into a protein, and therefore the insertion of the target sequence into the CVB3-WT genome is unlikely to affect virus RNA translation in the host cells and the virus RNA translation would be performed appropriately. Accordingly, protein synthesis and virus particle replication proceed and the virus can proliferate to enable the antitumor effects to be exhibited on the cancer cells.

Also, if the position at which the polynucleotide is inserted is between positions 7304 and 7305 inside the 3' UTR region of the CVB3-WT genome, replication is more unlikely to be hindered during the virus replication within the host cells.

The position between the positions 7304 and 7305 is inside the 3' UTR region of the CVB3-WT genome and is shifted by four bases downstream from a base sequence constituting a termination codon that terminates translation of the CVB3-WT genome into proteins (positions 7298, 7299, and 7300 constitute the termination codon). That is, due to being a position inside the 3' UTR region and close to the termination codon, translation can be ended appropriately while retaining a three-dimensional structure of the 3' UTR necessary for replication. Consequently, the virus can proliferate in the cancer cells and destroy the cancer cells more stably.

Also, if the position at which the polynucleotide is inserted is between positions 742 and 743 inside the 5' UTR region of the CVB3-WT genome, replication is more unlikely to be hindered during the virus replication within the host cells. Also, the state in which the polynucleotide is inserted in the CVB3-WT genome is maintained more readily and the polynucleotide can be made more unlikely to be removed from the genome.

The position between the positions 742 and 743 is inside the 5' UTR region of the CVB3-WT genome and corresponds to being immediately upstream a base sequence constituting an initiation codon that initiates the translation of the CVB3-WT genome into proteins (positions 743, 744, and 745 constitute the initiation codon). That is, due to being a position inside the 5' UTR region and adjacent the initiation codon, translation can be ended appropriately while retaining a three-dimensional structure of the 5' UTR necessary for replication. Also, the polynucleotide inserted in the 5' UTR region was less likely to become detached from the genome than the polynucleotide inserted in the 3' UTR region. Consequently, the virus can be hindered from proliferating in normal cells and the virus can efficiently proliferate in the cancer cells and destroy the cancer cells more stably.

Also, if a plurality of the polynucleotides constituted of the target sequence are inserted, a probability, in tissue in which the miRNA is present, of a RISC complex containing the miRNA binding to the target sequence can be increased to enable deviation from the miRNA to be avoided even when further virus genome mutation occurs, and the tissue-specific virus proliferation suppression can thus be further ensured.

Also, if the inserted polynucleotide is (a) or (b) shown below or a polynucleotide constituted of a sequence with which one to several nucleotides are deleted, substituted, or added with respect to (a) or (b), it would be that with which four target sequences for miR-34a or miR-34c are aligned with spacer sequences in between. The proliferation of the virus can thereby be suppressed more reliably in tissue in which miR-34a or miR-34c is present. Also, in tissue in which miR-34a or miR-34c is not present, that is, in the cancer cell, the virus can proliferate to enable the antitumor effects to be exhibited selectively. Here, the region in which the polynucleotide is inserted includes an arrangement constituted of just the inside of the 5' UTR region of the CVB3-WT genome, an arrangement constituted of just the inside of the 3' UTR region of the CVB3-WT genome, and an arrangement constituted of both the inside of the 5' UTR region and the inside of the 3' UTR region of the CVB3-WT genome.

(a) ACA ACC AGC TAA GAC ACT GCC AcgatA CAA CCA

GCT AAG ACA CTG CCA acc ggt ACA ACC AGC TAA GAC

ACT GCC AtcacA CAA CCA GCT AAG ACA CTG CCA (b) GCA ATC AGC TAA CTA CAC TGC CTc gat GCA ATC AGC TAA CTA CAC TGC CTaccggtG CAA TCA GCT AAC TAC ACT GCC TtcacG CAA TCA GCT AAC TAC ACT GCC T Also, if the polynucleotide is inserted in each of the inside of the 5' UTR region and the inside of the 3' UTR region of the CVB3-WT genome, this would mean that the inserted number of target sequences for miR-34a or miR-34c is increased and the proliferation of the virus can be suppressed even more reliably in tissue in which miR-34a or miR-34c is present. Also, even if the inserted polynucleotide becomes detached from the genome in one of the regions inside the 5' UTR region or inside the 3' UTR region, by the polynucleotide inserted in the other region being present, the proliferation of the virus can be suppressed stably in tissue in which miR-34a or miR-34c is present.

Also, if the tissue-specific miRNA includes at least one of miR-1 and miR-217, the proliferation of the gene-modified coxsackievirus can be suppressed tissue-specifically in the pancreas, the liver, or muscle tissue. That is, undesirable actions that occur when CVB3-WT is introduced into cells of the pancreas, the liver, or muscle tissue can be reduced or deterred.

Also, if the polynucleotide is (c) or (d) shown below or is a polynucleotide constituted of a sequence with which one to several nucleotides are deleted, substituted, or added with respect to (c) or (d), a polynucleotide constituted of two target sequences for miR-34a and two target sequences for miR-217 or a polynucleotide constituted of two target sequences for miR-34c and two target sequences for miR-217 is inserted in the CVB3-WT genome as the sequences targeted by miRNA. The proliferation of the virus can thereby be suppressed not just in tissue in which miR-34a or miR-34c is present but also in tissue in which miR-217 is present. Consequently, the safety in using the gene-modified coxsackievirus can be increased further. In particular, when CVB3-WT is used, the pancreas is where undesirable side effects occur strongly, and because high expression of miR-217 in the pancreas is seen, the polynucleotide suppresses the occurrence of side effects in the pancreas to contribute to improvement of safety. In the polynucleotide sequences here, spacer sequences are interposed between individual target sequences. Also, here, the region in which the polynucleotide is inserted includes an arrangement constituted of just the inside of the 5' UTR region of the CVB3-WT genome, an arrangement constituted of just the inside of the 3' UTR region of the CVB3-WT genome, and an arrangement constituted of both the inside of the 5' UTR region and the inside of the 3' UTR region of the CVB3-WT genome.

(c) ACA ACC AGC TAA GAC ACT GCC AcgatA CAA CCA

GCT AAG ACA CTG CCA acc ggt TCC AAT CAG TTC CTG

ATG CAG TAtcac TCC AAT CAG TTC CTG ATG CAG TA (d) GCA ATC AGC TAA CTA CAC TGC CTc gat GCA ATC AGC TAA CTA CAC TGC CTaccggtT CCA ATC AGT TCC TGA TGC AGT AtcacT CCA ATC AGT TCC TGA TGC AGT A Also, if the polynucleotide is inserted in each of the inside of the 5' UTR region and the inside of the 3' UTR region of the CVB3-WT genome, this would mean that the numbers of inserted target sequences for miR-34a and miR-217 or for miR-34c and miR-217 are increased and the proliferation of the virus can be suppressed even more reliably in tissue in which miR-34a and miR-217 or miR-34c and miR-217 are present. Also, even if the inserted polynucleotide becomes detached from the genome in one of the regions inside the 5' UTR region or inside the 3' UTR region, by the polynucleotide inserted in the other region being present, the proliferation of the virus can be suppressed stably in tissue in which miR-34a and miR-217 or miR-34c and miR-217 are present.

Also, if the polynucleotide is (e) or (f) shown below or a sequence with which one to several nucleotides are deleted, substituted, or added with respect to (e) or (f), a polynucleotide constituted of two target sequences for miR-34a and two target sequences for miR-1 or a polynucleotide constituted of two target sequences for miR-34c and two target sequences for miR-1 is inserted in the CVB3-WT genome as the sequence targeted by miRNA. The proliferation of the virus can thereby be suppressed not just in tissue in which miR-34a or miR-34c is present but also in tissue in which miR-1 is present. Consequently, the safety in using the gene-modified coxsackievirus can be increased further. In the polynucleotide sequences here, spacer sequences are interposed between individual target sequences. Also, here, the region in which the polynucleotide is inserted includes an arrangement constituted of just the inside of the 5' UTR region of the CVB3-WT genome, an arrangement constituted of just the inside of the 3' UTR region of the CVB3-WT genome, and an arrangement constituted of both the inside of the 5' UTR region and the inside of the 3' UTR region of the CVB3-WT genome.

(e) ACA ACC AGC TAA GAC ACT GCC AcgatA CAA CCA

GCT AAG ACA CTG CCA acc ggt ATA CAT ACT TCT TTA

CAT TCC AtcacA TAC ATA CTT CTTTAC ATT CCA (f) GCA ATC AGC TAA CTA CAC TGC CTc gat GCA ATC AGC TAA CTA CAC TGC CTaccggtA TAC ATA CTT CTTTAC ATT CCA tcacAT ACA TAC TTC TTT ACA TTC CA Advantageous Effects of Invention The gene-modified coxsackievirus according to the present invention is applicable in the field of oncolytic virotherapy of treating cancers and is excellent in antitumor effects and safety.

Also, a pharmaceutical composition according to the present invention is applicable in the field of oncolytic virotherapy of treating cancers and is excellent in antitumor effects and safety.

BRIEF DESCRIPTION OF DRAWINGS

FIG. 3 is an outline diagram showing the miR-34a sequence and the miR-34c sequence.

FIG. 6 shows a sequence where four target sequences for miR-34c are inserted between positions 742 and 743 bp inside the 5' UTR of the CVB3-WT genome.

FIG. 16 is a graph of evaluation of cell viabilities after 72 hours of cancer cells (MOI=0.001) and normal cells (MOI=0.1) upon infection with CVB3-WT, CVB3-miR-34aT-3, CVB3-miR-34cT-3, CVB3-miR-34aT-53, and CVB3-34a&217T-53.

DESCRIPTION OF EMBODIMENTS

Figure 1:
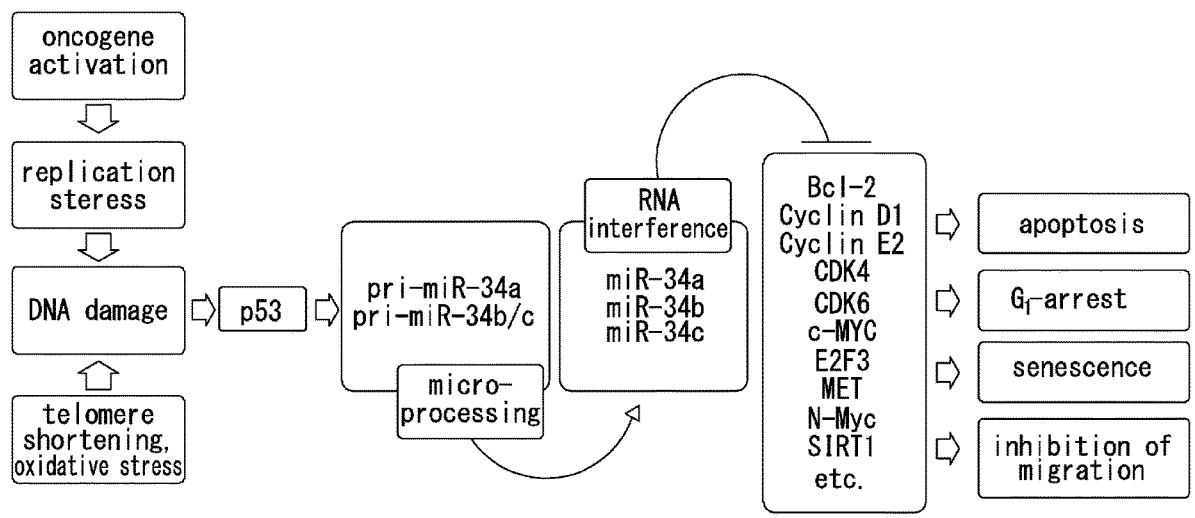
FIG. 1 is an outline block diagram showing expression of the miR-34 family and involvement in cell cycle and so forth.
Figure 2:
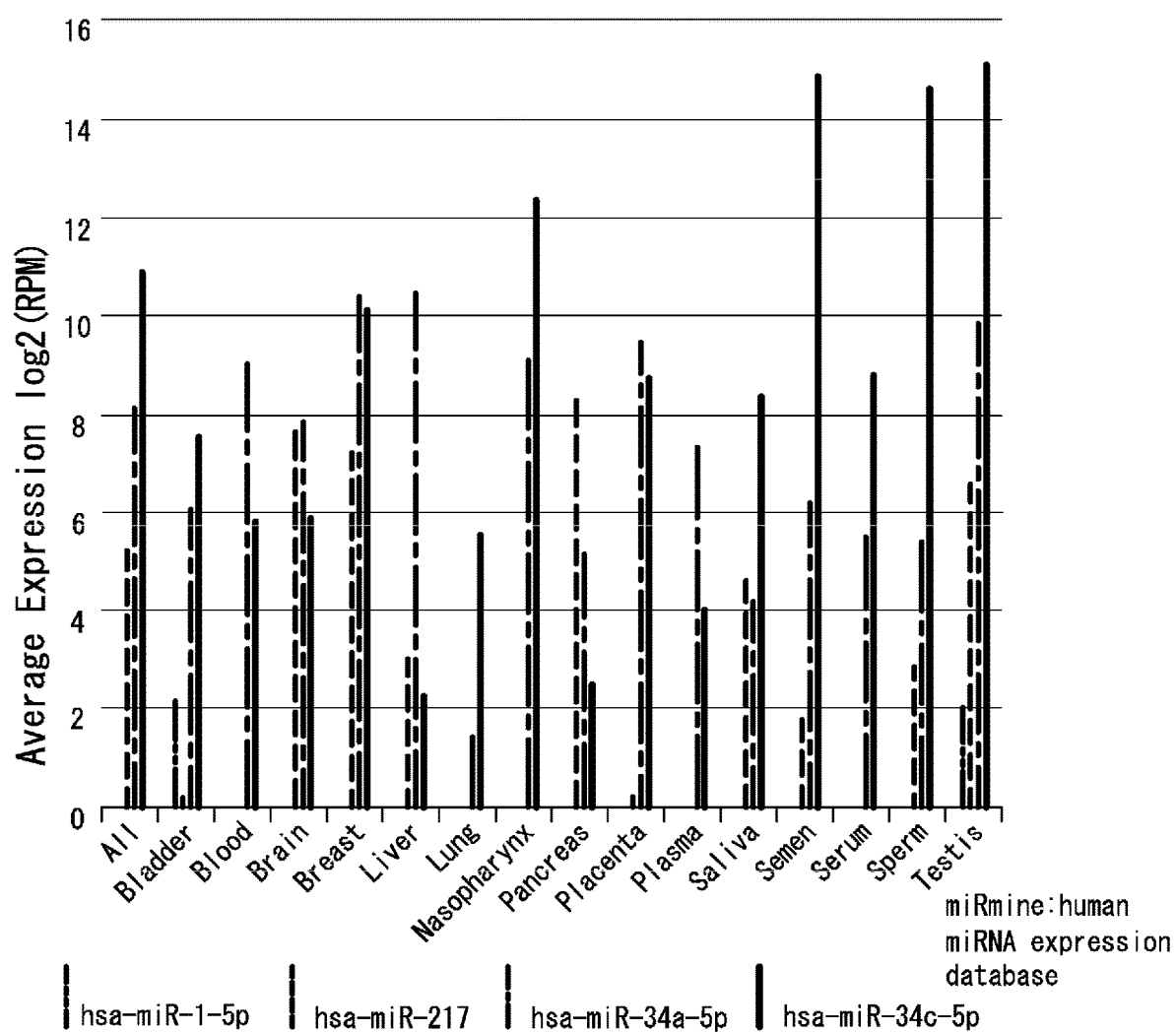
FIG. 2 is a graph showing expression amounts of respective miRNAs (miR-1, miR-217, miR-34a, and miR-34c) in respective tissues in a human living body.

When, in regard to the present invention, a numerical range is expressed as "X to Y," the range includes the values X and Y at both ends. When used in regard to the present invention, "A and/or B" means (i) at least one of A and B, or (ii) at least one of A or at least one of B.

[Gene-Modified Coxsackievirus]

<Improvement of Safety of CVB3 by Insertion of miR Target Sequence>

One aspect of a gene-modified coxsackievirus provided by the present invention is a gene-modified coxsackievirus that contains a mutated genome with a coxsackievirus wild-type (CVB3-WT) genome inserted with at least one polynucleotide constituted of a target sequence for a tissue-specific microRNA (miRNA). Such a gene-modified coxsackievirus can be tissue-specifically suppressed in proliferation.

A normal-cell-specific miRNA (and its target sequence) used in the present invention is at least one of either of miR-34a and miR-34c. miR-34a or miR-34c is a member of the miR-34 family that has been seen to be highly expressed in normal cells all over the body. Just one of miR-34a and miR-34c may be used or the two may be used in combination.

The miR-34a sequence (SEQ ID NO: 1) and the miR-34c sequence (SEQ ID NO: 2) are shown in FIG. 3.

With the present invention, a position at which the target sequence for the normal-cell- or tissue-specific miRNA is inserted is preferably inside a 5' UTR region or inside a 3' UTR region of the CVB3-WT genome. Also, the position at which the target sequence for the normal-cell- or tissue-specific miRNA is inserted is more preferably a region in each of inside the 5' UTR region and inside the 3' UTR region of the CVB3-WT genome.

Also, if the position at which the target sequence for the tissue-specific miRNA is inserted is inside the 3' UTR region of the CVB3-WT genome, the position is more preferably more upstream than position 7344 or more downstream than position 7345 of the CVB3-WT genome and is even more preferably between positions 7304 and 7305.

According to studies by the present inventors thus far, gene-modified CVB3 with the target sequence inserted between 7304 and 7305 bp was seen to proliferate in HeLa cells, which are general CVB3-producing cells, proliferation was not seen with gene-modified CVB3 with the target sequence inserted between 7344 and 7345 bp. Also, the same phenomena were seen with HeLa cells in which expression of miRNA was suppressed. Therefore, as stated above, the position at which the target sequence for the tissue-specific miRNA is inserted is preferably inside the 3' UTR region of the CVB3-WT genome, more preferably more upstream than the position 7344 or more downstream than the position 7345 of the CVB3-WT genome, and even more preferably between the positions 7304 and 7305.

Also, if the position at which the target sequence for the tissue-specific miRNA is inserted is inside the 5' UTR region of the CVB3-WT genome, the position is preferably between positions 742 and 743 of the CVB3-WT genome.

Also, the number of inserted target sequences for miR-34a or miR-34c is preferably plural, for example, two to six.

In an especially preferable aspect, the inserted polynucleotide is (a) or (b) shown below. Or, it is a polynucleotide constituted of a sequence with which one to several nucleotides are deleted, substituted, or added with respect to (a) or (b) and is capable of functioning in the same manner as (a) or (b), that is, is capable of suppressing proliferation specifically in normal cells when inserted in at least one of between the positions 742 and 743 of the CVB3-WT genome (5' UTR region), between the positions 7304 and 7305 of the CVB3-WT genome (3' UTR region), and the respective regions between the positions 742 and 743 of the CVB3-WT genome (5' UTR region) and between the positions 7304 and 7305 of the CVB3-WT genome (3' UTR region) to arrange the gene-modified coxsackievirus. Or, the inserted polynucleotide is a polynucleotide constituted of a sequence having a sequence identity of at least 90%, preferably 95%, more preferably 98%, and even more preferably 99% with the nucleotide sequence indicated in (a) or (b) and is capable of functioning in the same manner as (a) or (b), that is, is capable of suppressing proliferation specifically in normal cells when inserted in each position of the CVB3-WT genome to arrange the gene-modified coxsackievirus.

(SEQ ID NO: 3)
(a) ACA ACC AGC TAA GAC ACT GCC AcgatA CAA CCA

GCT AAG ACA CTG CCA acc ggt ACA ACC AGC TAA GAC

ACT GCC AtcacA CAA CCA GCT AAG ACA CTG CCA (SEQ ID NO: 4)
(b) GCA ATC AGC TAA CTA CAC TGC CTc gat GCA ATC AGC TAA CTA CAC TGC CTaccggtG CAA TCA GCT AAC TAC ACT GCC TtcacG CAA TCA GCT AAC TAC ACT GCC T Methods for obtaining a polynucleotide having a sequence with which one to several nucleotides are deleted, substituted, or added with respect to a certain nucleotide sequence and methods for calculating sequence identity related to a nucleotide sequence (for example, sequence identity can be calculated using a BLAST algorithm) is well known to those skilled in the art. The same applies to nucleotide sequences indicated below.

Also, from a standpoint of reducing undesirable actions of CVB3-WT in respective tissues, the tissue-specific miRNA (and its target sequence) used in the present invention may include at least one of miR-1 and miR-217. miR-217 is said to be expressed specifically in the pancreas and miR-1 is said to be expressed specifically in muscle tissue and normal cells. miR-1 and miR-217 are used in combination with at least one of miR-34a and miR-34c. Also, miR-1 and miR-217 may be combined.

Although any number can be selected as the number of inserted target sequences for miR-1 or miR-217 as long as the intended effects are exhibited, it is preferably plural, for example, two to six.

Figure 7:
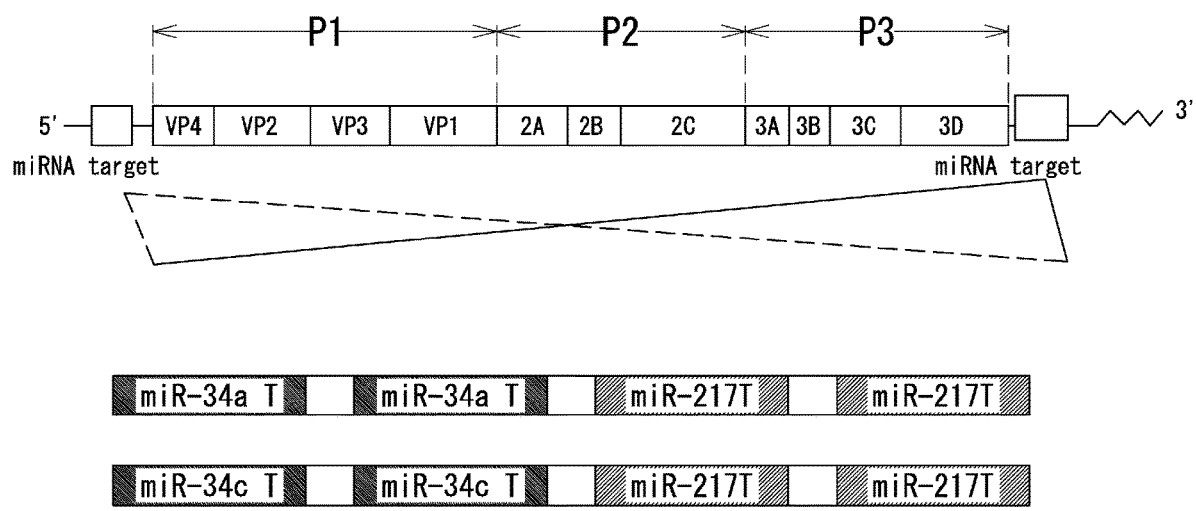
FIG. 7 is an outline diagram of CVB3 carrying miR-34a and miR-217 target sequences or miR-34c and miR-217 target sequences.

Also, in another especially preferable aspect, the inserted polynucleotide is (c) or (d) shown below. Or, it is a polynucleotide constituted of a sequence with which one to several nucleotides are deleted, substituted, or added with respect to (c) or (d) and is capable of functioning in the same manner as (c) or (d), that is, is capable of suppressing proliferation specifically in normal cells when inserted in at least one of between the positions 742 and 743 of the CVB3-WT genome (5' UTR region), between the positions 7304 and 7305 of the CVB3-WT genome (3' UTR region), and each of between the positions 742 and 743 of the CVB3-WT genome (5' UTR region) and between the positions 7304 and 7305 of the CVB3-WT genome (3' UTR region) to arrange the gene-modified coxsackievirus. Also, the inserted polynucleotide is capable of suppressing proliferation tissue-specifically in the pancreas (see FIG. 7). Or, the inserted polynucleotide is a polynucleotide constituted of a sequence having a sequence identity of at least 90%, preferably 95%, more preferably 98%, and even more preferably 99% with the nucleotide sequence indicated in (c) or (d) and is capable of functioning in the same manner as (c) or (d), that is, is capable of suppressing proliferation specifically in normal cells when inserted in each position of the CVB3-WT genome to arrange the gene-modified coxsackievirus. Also, the inserted polynucleotide is capable of suppressing proliferation tissue-specifically in the pancreas.

(SEQ ID NO: 5)
(c) ACA ACC AGC TAA GAC ACT GCC AcgatA CAA CCA

GCT AAG ACA CTG CCA acc ggt TCC AAT CAG TTC CTG

ATG CAG TAtcac TCC AAT CAG TTC CTG ATG CAG TA (SEQ ID NO: 6)
(d) GCA ATC AGC TAA CTA CAC TGC CTc gat GCA ATC AGC TAA CTA CAC TGC CTaccggtT CCA ATC AGT TCC TGA TGC AGT AtcacT CCA ATC AGT TCC TGA TGC AGT A Also, in another especially preferable aspect, the inserted polynucleotide is (e) or (f) shown below. Or, it is a polynucleotide constituted of a sequence with which one to several nucleotides are deleted, substituted, or added with respect to (e) or (f) and is capable of functioning in the same manner as (e) or (f), that is, is capable of suppressing proliferation specifically in normal cells and tissue when inserted in at least one of between the positions 742 and 743 of the CVB3-WT genome (5' UTR region), between the positions 7304 and 7305 of the CVB3-WT genome (3' UTR region), and each of between the positions 742 and 743 of the CVB3-WT genome (5' UTR region) and between the positions 7304 and 7305 of the CVB3-WT genome (3' UTR region) to arrange the gene-modified coxsackievirus. Also, the inserted polynucleotide is capable of suppressing proliferation tissue-specifically in muscle tissue. Or, the inserted polynucleotide is a polynucleotide constituted of a sequence having a sequence identity of at least 90%, preferably 95%, more preferably 98%, and even more preferably 99% with the nucleotide sequence indicated in (e) or (f) and is capable of functioning in the same manner as (e) or (f), that is, is capable of suppressing proliferation specifically in normal cells when inserted in each position of the CVB3-WT genome to arrange the gene-modified coxsackievirus.

Also, the inserted polynucleotide is capable of suppressing proliferation tissue-specifically in muscle tissue.

(SEQ ID NO: 7)
(e) ACA ACC AGC TAA GAC ACT GCC AcgatA CAA CCA

GCT AAG ACA CTG CCA acc ggt ATA CAT ACT TCT TTA

CAT TCC AtcacA TAC ATA CTT CTT TAC ATT CCA (SEQ ID NO: 8)
(f) GCA ATC AGC TAA CTA CAC TGC CTc gat GCA ATC AGC TAA CTA CAC TGC CTaccggtA TAC ATA CTT CTT TAC ATT CCA tcacAT ACA TAC TTC TTT ACA TTC CA

[Preparation of Gene-Modified Virus, Etc.]

The gene-modified virus of the present invention can be prepared by genetically manipulating CVB3-WT. CVB3-WT can be isolated from a sample or the like by a known virus isolation method. Examples of the virus isolation method include centrifugation, proliferation of the virus in cultured cells, and so forth. Once the gene-modified coxsackievirus is prepared, the gene-modified coxsackievirus can be proliferated using various molecular biological methods for virus production.

CVB3 that is to be the starting point of gene-modification may be biologically selected by culturing a naturally occurring virus over several passages in a cell line such that the virus acquires a high infectivity for cancer cells. Examples of a cell line suitable for the biological selection include cancer cell lines that express CAR, DAF, and so forth.

For evaluation of the gene-modified coxsackievirus prepared according to the present invention, various aspects, such as safety, efficacy, and titer, can be evaluated by various in vitro or in vivo means well known to those skilled in the art. For example, aggressiveness against cancer cells (oncolytic property or cytotoxicity) can be confirmed by testing survival of a cancer cell line exposed to CVB3. Examples of a method for testing the survival of a cell line include a method of staining fixed cells with a staining solution and quantifying the number of stained live cells, a crystal violet method, a method of quantifying an apoptosis-specific marker, and so forth. As a result of using any of the aforementioned methods on a cell line of cancer cells incubated with CVB3 to quantify the cancer cells surviving after a predetermined time, the cancer cells killed by the cytotoxicity due to infection by CVB3 can be quantified.

Figure 8:
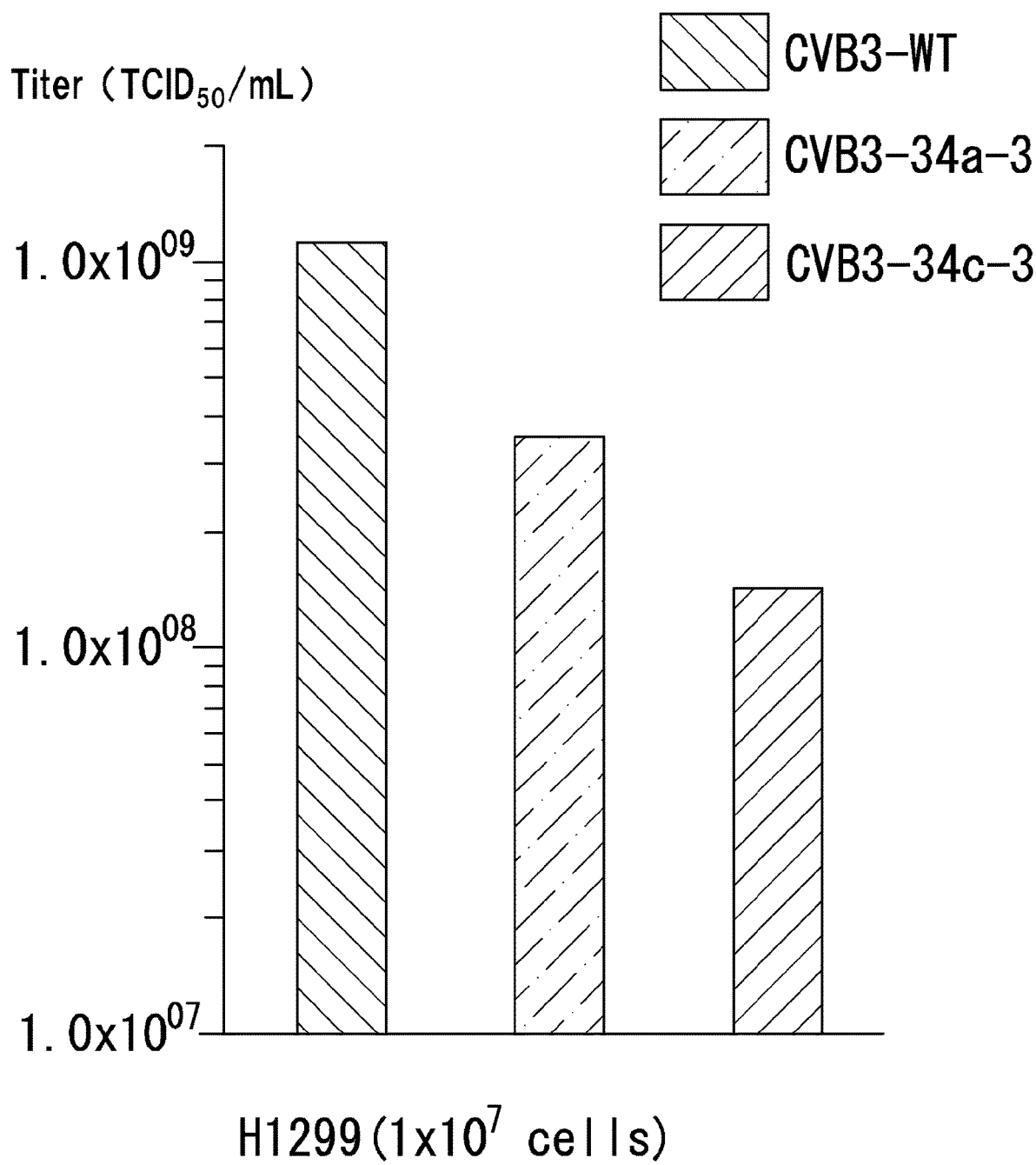
FIG. 8 is a graph showing test results of measuring virus titers in lung cancer cell line NCI-H1299 (H1299) cells using CVB3-WT and gene-modified CVB3s produced in H1299 cells.

When, in regard to measurements of production and titer of the gene-modified CVB3 (inserted with the target sequence for miR-34a or the target sequence for miR-34c), the present inventors measured the virus titer in H1299 cells using the gene-modified CVB3 produced in H1299 cells, the results indicated that, although its virus titer is slightly lower than the virus titer of CVB3-WT, the gene-modified CVB3 has a sufficient virus titer (see FIG. 8). Therefore, in one aspect of the present invention, H1299 cells are appropriate for the production of the gene-modified virus and virus titer measurement. By the present invention, for titer measurement or proliferation of the gene-modified coxsackievirus, use of cells with which an expression amount of the corresponding normal-cell-specific miRNA is not high (for example, H1299 cells) is proposed.

[Pharmaceutical Composition]
<Indication of Treatment>

One aspect of a pharmaceutical composition provided by the present invention contains the above-described gene-modified CVB3 as an active ingredient. The types of cancer to be an object of treatment with the pharmaceutical composition are not particularly limited and include solid cancers and fluid cancers. CVB3 has cytotoxicity against cancer cells of solid cancers and fluid cancers. The cytotoxicity of CVB3 against cancer cells is based on lysis of cancer cells upon infection of the cancer cells and replication in the cytoplasm of the cancer cells by the virus or on apoptosis induced by activation of caspase in the cancer cells caused by infection by the virus. CVB3 can recognize CAR on the cell surface and infect the cell. "Treatment (to treat)" as referred to in the present invention in relation to a disease or condition includes preventive treatment and curative treatment.

CVB3 has cytotoxicity against cancer cells of solid cancers and fluid cancers, and in regard to solid cancers, cancer cells with which especially potent cytotoxicity is induced are cells of a cancer selected from the group consisting of small cell lung cancer, non-small cell lung cancer, lung squamous cell cancer, malignant mesothelioma, colon cancer, colorectal cancer, esophageal cancer, hypopharyngeal cancer, human B lymphoma, breast cancer, and uterine cervix cancer. The pharmaceutical composition according to the present embodiment is thus preferably applied to a cancer selected from the group consisting of small cell lung cancer, non-small cell lung cancer, lung squamous cell cancer, malignant mesothelioma, colon cancer, colorectal cancer, esophageal cancer, hypopharyngeal cancer, human B lymphoma, breast cancer, and uterine cervix cancer as an object of treatment.

Lung cancer is a cancer with which the number of affected individuals is of high rank. The pharmaceutical composition according to the present embodiment can contribute to the treatment of more lung cancer patients. In Japan, where Western eating habits are established, colon cancer and colorectal cancer morbidities are increasing and mortalities of these cancers are also increasing. The pharmaceutical composition according to the present embodiment increases the choices of curative drugs for colon cancer and colorectal cancer, and this is beneficial for the patients. The recurrence rate of esophageal cancer after surgical resection is as high as 30 to 50%, and the sensitivity thereof to existing drugs is low. The pharmaceutical composition according to the present embodiment can be anticipated to improve treatment results of esophageal cancer.

Also, the pharmaceutical composition according to the present embodiment exhibits potent cytotoxicity against CDDP-resistant, gefitinib-resistant, or oxaliplatin-resistant cancer cells. Therefore, a treatment that is effective against so-called intractable cancers that exhibit resistance to these anticancer agents can be provided.

When containing CVB3, the pharmaceutical composition according to the present embodiment exhibits potent cytotoxicity also against cancer stem cells. Cancer stem cells are considered to be one of the causes of relapse of cancer, and the composition is thus useful for prevention of metastasis and relapse of cancer.

<Dosage Form, Usage, and Dosage>

Also, the pharmaceutical composition according to the present embodiment can be adopted in various dosage forms and various administration routes. That is, the pharmaceutical composition according to the present embodiment can also be a topical preparation or a preparation for systemic administration. For example, it can be arranged as an injection or a drip and administered by intratumoral administration, intravenous administration, intrathoracic administration, or intraperitoneal administration in accordance with the type of cancer. In particular, in many cases of gastrointestinal cancers, such as esophageal cancer and colon cancer, the pharmaceutical composition can be injected directly into a tumor tissue while visually observing the tumor tissue with an endoscope or the like. In such a case, since the injection site can be confirmed with the endoscope or the like, there is also provided an advantage that even if bleeding occurs, it is easily treated. Besides the above, the composition may be administered orally or it may be administered intramuscularly or subcutaneously or via the rectum, vagina, nasal cavity, or the like.

The pharmaceutical composition according to the present embodiment may be arranged to contain a carrier, diluent, auxiliary agent, and so forth in addition to the gene-modified CVB3. As the carrier, for example, a liposome, micelle, and so forth are preferred. The liposome contains a combination of a lipid with a steroid or a steroid precursor that contributes to membrane stability. As the lipid in this case, a phosphatidyl compound, such as phosphatidylglycerol, phosphatidylcholine, phosphatidylserine, sphingolipid, phosphatidylethanolamine, cerebroside, and ganglioside, can be cited. CVB3 coated with the liposome or micelle can reduce the immune response of a host.

As examples of the diluent, desalted water, distilled water, physiological saline, and so forth can be cited. As examples of the auxiliary agent, vegetable oils, cellulose derivatives, polyethylene glycol, fatty acid esters, and so forth can be cited.

In the case of oral administration, the pharmaceutical composition may contain a sweetener, disintegrating agent, diluent, coating agent, preservative, and so forth.

The pharmaceutical composition according to the present embodiment is administered such that an amount of CVB3 would be sufficient for treatment of cancer. A dosage is determined based on body weight, age, and sex of a patient, size of tumor tissue, and so forth. For example, when the pharmaceutical composition is arranged as a liquid preparation, it is sufficient that $1 \times 10^2$ to $1 \times 10^{10}$ $TCID_{50}$ (50% tissue culture infectious dose) of CVB3 is contained in 1 ml of the liquid formulation. Preferably, it is sufficient that $1 \times 10^5$ $TCID_{50}$ or more of CVB3 is contained in 1 ml of the liquid preparation. The pharmaceutical composition may be administered in one dose or may be administered over a plurality of doses. The pharmaceutical composition may be continuously administered as a sustained release preparation.

<Combined Use with Other Preparations>

The pharmaceutical composition according to the present embodiment may be used in combination with an anticancer agent. By combined use with the anticancer agent that differs in action mechanism from the pharmaceutical composition, improvement in antitumor effect can be anticipated. The anticancer agent is not particularly limited, and those used for treatment of small cell lung cancer, non-small cell lung cancer, lung squamous cell cancer, malignant mesothelioma, colon cancer, colorectal cancer, esophageal cancer, hypopharyngeal cancer, human B lymphoma, uterine cervix cancer, pancreatic cancer, and so forth are desirable. Specific anticancer agents include CDDP (cisplatin), gefitinib, oxaliplatin, and so forth.

[Others]

The pharmaceutical composition according to the embodiment of the present invention may contain, as an active ingredient, a polynucleotide derived from CVB3 (including the gene-modified CVB3; the same applies below) capable of infecting cancer cells. The CVB3-derived polynucleotide may be a virus RNA directly isolated from CVB3, a synthetic RNA, or a cDNA corresponding to abase sequence of an isolated virus RNA, respectively. Any method can be used to isolate the virus RNA. Examples of the method for isolating the virus RNA include a method based on use of phenol/chloroform extraction and so forth. Also, the polynucleotide may be a virus plasmid or an expression vector containing a polynucleotide for producing a virus. The expression vector includes, for example, a plasmid that can express an RNA encoding a virus protein required for producing the virus. The expression vector may contain a transcription regulatory/control sequence that is functionally ligated with the inserted polynucleotide. The transcription regulatory/control sequence referred to here is, for example, a promoter for initiating transcription, an expression control element for enabling binding of a ribosome to a transcribed mRNA, and so forth.

As the expression vector, for example, pSV2neo, pEF-PGKpuro, pTk2, non-replicating adenovirus shuttle vector, cytomegalovirus promoter, and so forth can be used. The cDNA that encodes the virus protein required for producing the virus can be prepared by reverse transcription of the virus RNA or a fragment thereof.

The pharmaceutical composition according to the present embodiment may contain, for example, a carrier such as a liposome, in addition to the polynucleotide derived from CVB3 capable of infecting cancer cells. The polynucleotide derived from CVB3 may contain, for example, the polynucleotide constituted of the sequence of SEQ ID NO: 1 or 2, and/or the polynucleotide constituted of any of the sequences of SEQ ID NOS: 3 to 8, 19, 20, 25, and 26.

Examples of the present invention shall now be described. However, the scope of the present invention is not limited by these examples.

The contents shown in Table 1 below are given as an example of kinds of target sequences for the tissue-specific miRNAs in the present invention and positions in the CVB3-WT genome at which the target sequences are inserted.

TABLE 1

| No. | name (Virus) | 5' UTR (between 742 & 743) | 3' UTR (between 7304 & 7305) |
|---|---|---|---|
| 1 | CVB3-34aT-3 | — | miR-34aT × 4 |
| 2 | CVB3-34cT-3 | — | miR-34cT × 4 |
| 3 | CVB3-34aT-5 | miR-34aT × 4 | — |
| 4 | CVB3-34cT-5 | miR-34cT × 4 | — |
| 5 | CVB3-34aT-53 | miR-34aT × 4 | miR-34aT × 4 |
| 6 | CVB3-34cT-53 | miR-34cT × 4 | miR-34cT × 4 |
| 7 | CVB3-34a&217T-53 | miR-34aT × 2 & miR-217T × 2 | miR-34aT × 2 & miR-217T × 2 |
| 8 | CVB3-34c&217T-53 | miR-34cT × 2 -217T × 2 | miR-34cT × 2 & miR-217T × 2 |

To describe the contents of Table 1, No., name of virus, kind of target sequence inserted between the positions 742 and 743 bp inside the genome 5' untranslated region (UTR) of CVB3-WT, and kind of target sequence inserted between the positions 7304 and 7305 bp inside the genome 3' untranslated region (UTR) of CVB3-WT are indicated from the left side of the table. For example, the virus of No. 7 (CVB3-34a&217T-53) is a modified virus with which a polynucleotide combining two target sequences for miR-34a and two target sequences for miR-217 is inserted in each of between the positions 742-743 bp inside the 5' UTR and between the positions 7304 and 7305 bp inside the 3' UTR. As the target sequences, a total of eight miRNA target sequences are inserted onto the genome. That is, the two target sequences for miR-34a and the two target sequences for miR-217 are inserted between the positions 742-743 bp inside the 5' UTR. Also, the two target sequences for miR-34a and the two target sequences for miR-217 are inserted between the positions 7304 and 7305 bp inside the 3' UTR.

EXAMPLES

I. Improvement in Safety of CVB3 by Insertion of miRNA Target Sequence

An object of the present research is to suppress proliferation of a gene-modified virus of oncolytic wild-type CVB3 (CVB-WT) in normal cells. The inventors inserted a target sequence for miR-34a or miR-34c in the genome 3' untranslated region (UTR) of the CVB3-WT, in particular, between 7304 and 7305 bp of the CVB3 genome to prepare a gene-modified virus. Also, the inventors inserted the target sequence for miR-34a or miR-34c in the genome 5' untranslated region (UTR) of the CVB3-WT, in particular, between 742 and 743 bp of the CVB3 genome to prepare a gene-modified virus. Further, the inventors inserted four target sequences for miR-34a or miR-34c or inserted a polynucleotide combining two target sequences for miR-34a and two target sequences for miR-217 in each of between the positions 742 and 743 bp inside the 5' UTR and between the positions 7304 and 7305 bp inside the 3' UTR of the CVB3-WT genome to prepare a gene-modified virus. A RISC complex having miR-34a, miR-34c, or miR-217 that is highly expressed in normal cells binds to the inserted target sequence for miR-34a, miR-34c, or miR-217 to inhibit translation of the virus protein and so forth to enable suppression of proliferation inside the normal cells.

I-1. Insertion of Target Sequences into CVB3 Genome and Virus Titers

The inventors made note of two miRNAs, namely, miR-34a and miR-34c that constitute the miR-34 family with which high expression is seen in normal cells all over the body and prepared two kinds of miRNA target sequences in each of which four target sequences for one of the miRNAs are ligated consecutively (miR-34aT×4+(miR-34aT×4−) and miR-34cT×4+(miR-34cT×4−)).

Also, an miRNA target sequence combining two target sequences for miR-34a and two target sequences for miR-217 (miR-34aT×2&miR-217T×2+(miR-34aT×2&miR-217T×2−)) was prepared.

Figure 4:
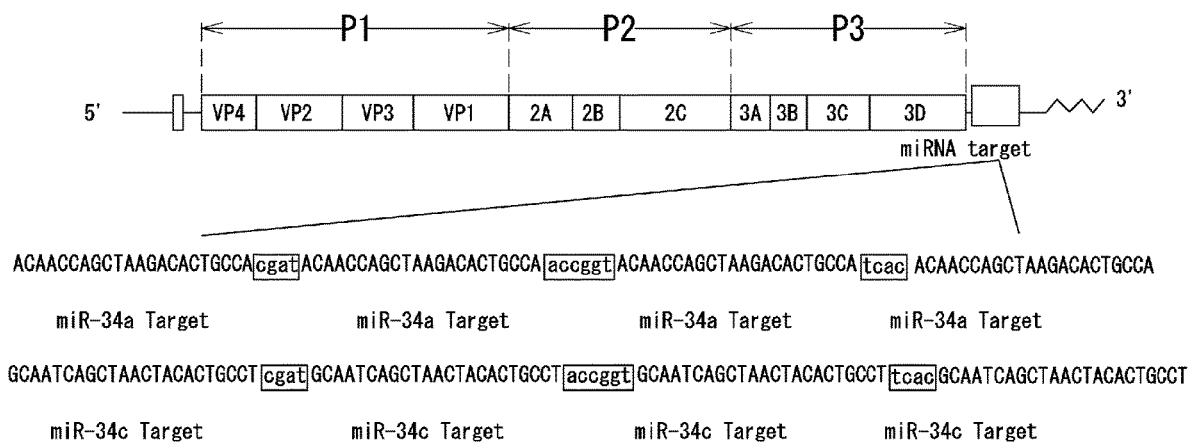
FIG. 4 is an outline diagram of CVB3 carrying anmiR-34a target sequence or anmiR-34c target sequence. The sequence shown in the figure is inserted between 7304 and 7305 bp of pBluescript II-CVB3 by the In-Fusion cloning method.
Figure 5:
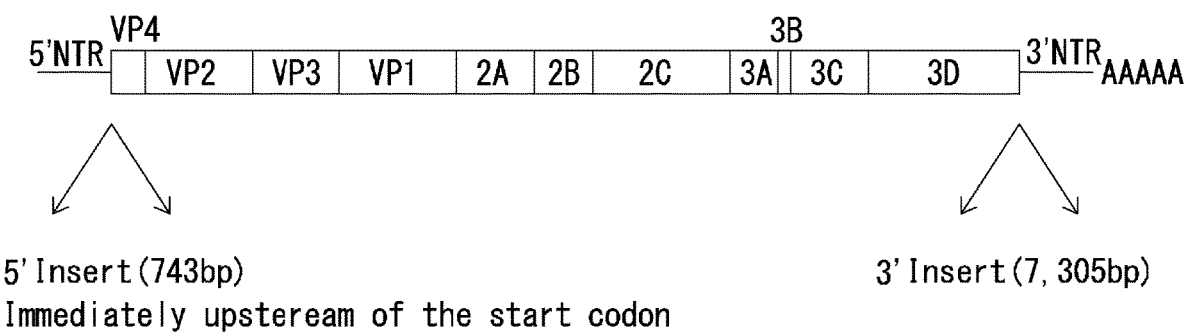
FIG. 5 is an outline diagram showing positions of insertion of target sequences into the inside of a 5' UTR region (between positions 742 and 743 bp) and the inside of a 3' UTR region (between positions 7304 and 7305 bp) on the CVB3 genome.

The target sequence for miR-34a and the target sequence for miR-34c were respectively inserted between 7304 and 7305 bp of the CVB3 genome. Also, the target sequence for miR-34a and the target sequence for miR-34c were respectively inserted between 742 and 743 bp of the CVB3 genome. Further, the target sequence for miR-34a and miR-217 was inserted in each of between 742 and 743 bp of the CVB3 genome and between 7304 and 7305 bp of the CVB3 genome. The insertion of the target sequences into the genome was performed using the In-Fusion cloning (Ta-KaRa Inc.) method (see FIG. 4, FIG. 5, and FIG. 6). The In-Fusion cloning method can be performed easily by purchasing a commercially available kit (TaKaRa Inc.). The respective gene-modified CVB3s (CVB3-miR-34aT and CVB3-miR-34cT) were both seen to proliferate in a lung cancer cell line (NCI-H1299 cells) and the preparation of the gene-modified CVB3s was successful. In addition, FIG. 6 is a diagram showing the position of insertion into the 5' UTR of the CVB3-WT genome and shows, as an example, the sequence where four target sequences for miR-34c are inserted between positions 742 and 743 bp inside the 5' UTR.

Hereinafter, unless noted in particular otherwise,
CVB3-34aT-3 refers to a virus in which four target sequences for miR-34a (the polynucleotide of SEQ ID NO: 3) are inserted in the 3' UTR, and
CVB3-34cT-3 refers to a virus in which four target sequences for miR-34c (the polynucleotide of SEQ ID NO: 4) are inserted in the 3' UTR.

Also, CVB3-34aT-5 refers to a virus in which four target sequences for miR-34a (the polynucleotide of SEQ ID NO: 3) are inserted in the 5' UTR, and
CVB3-34aT-53 refers to a virus in which four target sequences for miR-34a (the polynucleotide of SEQ ID NO: 3) are inserted in each of the 5' UTR and the 3' UTR.

Further, CVB3-34a&217T-53 refers to a virus in which a polynucleotide constituted of two target sequences for miR-34a and two target sequences of miR-217 (the polynucleotide of SEQ ID NO: 25) is inserted in each of the 5' UTR and the 3' UTR.

Also, CVB3-1&217T refers to the virus in which a polynucleotide constituted of two target sequences for miR-1 and two target sequences of miR-217 (the polynucleotide of SEQ ID NO: 29) is inserted in the 3' UTR.

Next, to evaluate virus titers of the gene-modified CVB3s, the virus titers were compared with that of CVB-WT. Here, virus production and titer were measured using H1299 cells. In more detail, the respective viruses of CVB3-WT, CVB3-34aT-3, and CVB3-34cT-3 were introduced into a non-virus-infected H1299 cell line to produce viruses. The produced viruses were recovered and a non-virus-infected H1299 cell line was infected therewith again to measure the virus titers. The respective virus titers of CVB3-34aT-3 and CVB3-34cT-3 in the H1299 cells, although slightly lower than the virus titer of CVB-WT, were of $TCID_{50}$/ml values exceeding $1.0×10^8$ and it was thus made clear that the viruses have sufficient titers to be subject to nonclinical tests (see FIG. 8).

I-2. Evaluation of Oncolytic Activities of Gene-Modified Viruses with Respect to Cancer Cells and Normal Cells Next, it was evaluated whether or not the respective viruses of CVB3-WT, CVB3-34aT-3, and CVB3-34cT-3 proliferate and have oncolytic effects in various cancer cells and normal cells. As the cancer cells, lung cancer cell lines of NSCLC (A549 cells and H1299 cells), a pancreatic cancer cell line of AsPC-1 cells, and a breast cancer cell line of ZR-75-1 cells were used, and as the normal cells, BEAS-2B cells, which are normal tracheal epithelial cells, and Het-1A cells, which are normal esophagus squamous cells, were used.

Figure 9:
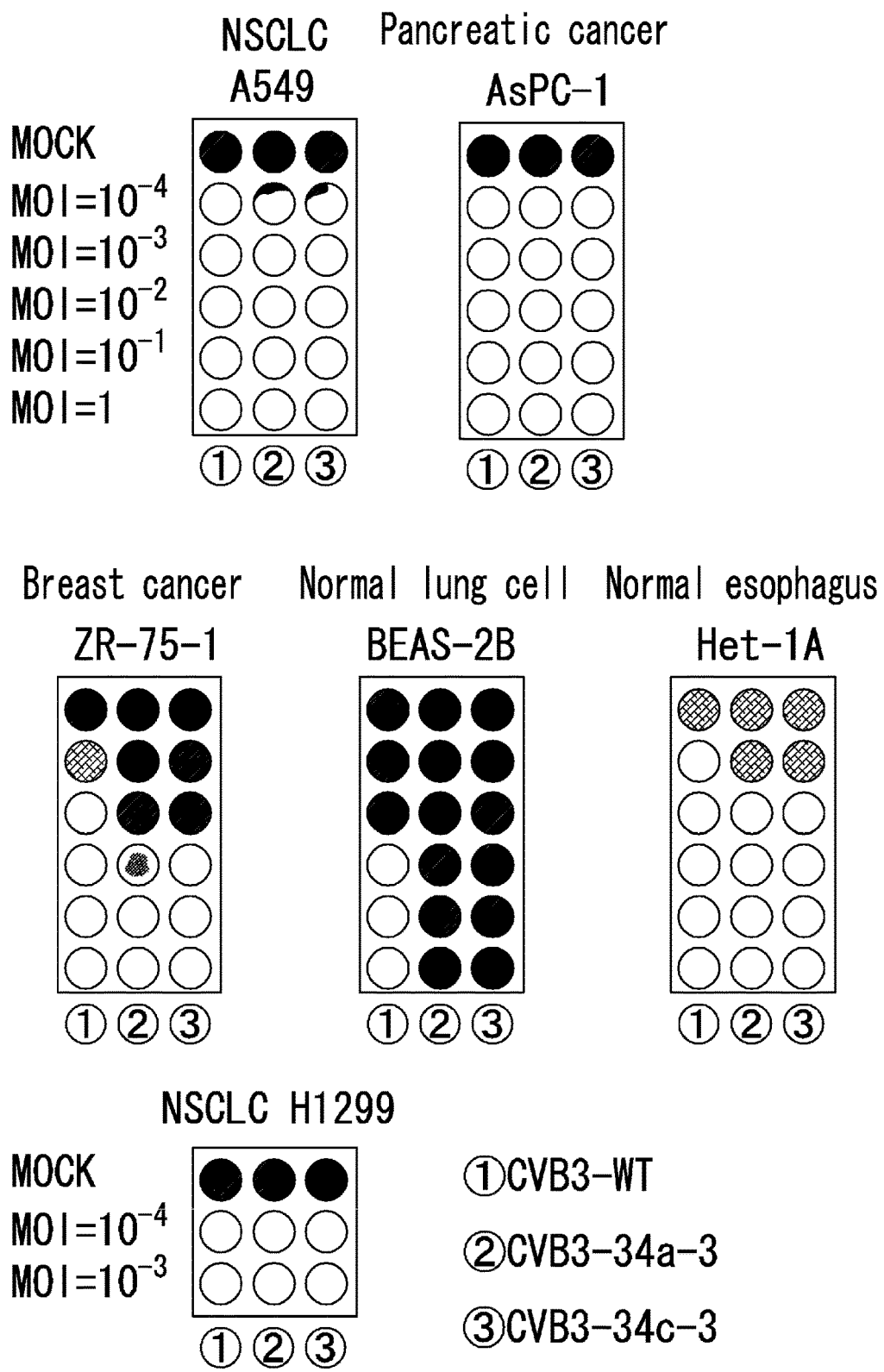
FIG. 9 is a schematic diagram showing whether or not CVB3-WT, CVB3-miR-34aT-3, and CVB3-miR-34cT-3 have oncolytic effects in cancer cells and normal cells.

Consequently, results indicating that CVB3-34aT-3 and CVB3-34cT-3 exhibit sufficient oncolytic effects in the respective cancer cells were obtained (see FIG. 9). In particular, CVB3-34aT-3 and CVB3-34cT-3 exhibited the same behavior as CVB3-WT in the A549 cells, H1299 cells, and AsPC-1 cells. On the other hand, with CVB3-34aT-3 and CVB3-34cT-3, differences in oncolytic effect with respect to CVB3-WT arose, and it was made clear that in the BEAS-2B cells, oncolytic effects are not seen even upon infection by virus amounts 100 times that of CVB3-WT (see FIG. 9). It was also made clear that in Het-1A cells as well, oncolytic effects are not seen even upon infection by virus amounts 10 times that of CVB3-WT (see FIG. 9).

From the above, it was made clear that CVB3-34aT-3 and CVB3-34cT-3 are capable of virus proliferation and exhibit oncolytic effects in the cancer cells. It was also made clear that these viruses, unlike CVB3-WT, do not exhibit oncolytic effects and are suppressed in virus proliferation in the normal cells.

Next, it was evaluated whether or not the respective viruses of CVB3-WT, CVB3-34aT-3, CVB3-34aT-5, CVB3-34aT-53, and CVB3-34a&217T-53 proliferate and have oncolytic effects in various cancer cells and normal cells. As the cancer cells, the abovementioned NSCLC (H1299 cells: ordinary) and NSCLC forcibly made by a known method to express miR-34a highly (H1299 cells: high expression) were used, and as the normal cells, the abovementioned BEAS-2B cells were used. In regard to the preparation of the H1299 cells forcibly made to express miR-34a highly, a known method was used and description of the preparation method shall thus be omitted.

Figure 10:
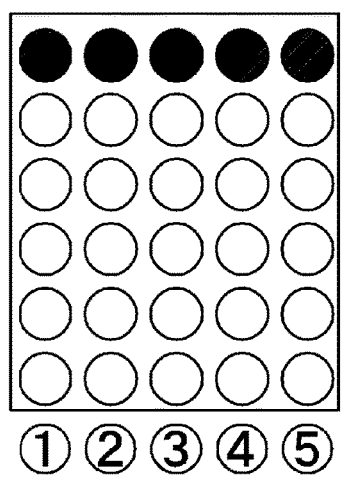
FIG. 10 is a schematic diagram showing whether or not CVB3-WT, CVB3-miR-34aT-3, CVB3-miR-34aT-5, CVB3-miR-34aT-53, and CVB3-34a&217T-53 have oncolytic effects in ordinary cancer cells, cancer cells made to highly express miRNA-34a, and normal cells.
Figure 10:
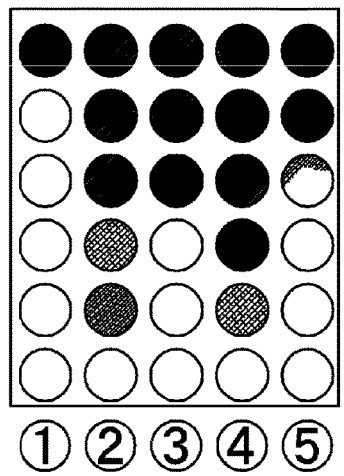
Figure 10:
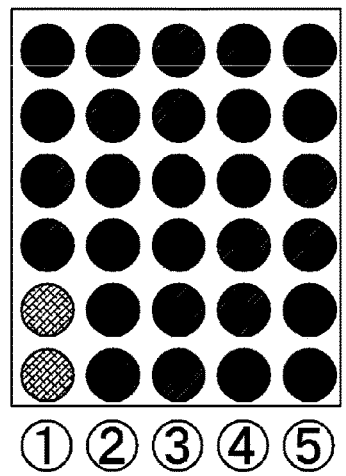

Consequently, results indicating that the respective viruses exhibit sufficient oncolytic effects in the ordinary H1299 cells were obtained (see upper diagram in FIG. 10). Also, in the H1299 cells made to express miR-34a highly, differences in oncolytic effect arose between CVB3-WT and other viruses, and it was made clear that oncolytic effects are not seen even upon infection by virus amounts 100 times that of CVB3-WT (see lower left diagram in FIG. 10). Differences in oncolytic effect arose between CVB3-WT and other viruses in the BEAS-2B cells as well, and whereas oncolytic effects were confirmed for CVB3-WT samples of high virus concentration (MOI=$10^{-1}$ and MOI=1), oncolytic effects were not confirmed for other viruses even with samples of the highest virus concentration (MOI=1) (see lower right diagram in FIG. 10).

From the above, it was made clear that CVB3-34aT-3, CVB3-34aT-5, CVB3-34aT-53, and CVB3-34a&217T-53 are capable of virus proliferation and exhibit oncolytic effects in the cancer cells. It was further made clear that these viruses, unlike CVB3-WT, do not exhibit oncolytic effects and are suppressed in virus proliferation in cancer cells forcibly made to express miR-34a highly and in the normal cells.

Next, it was evaluated whether or not the respective viruses of CVB3-WT, miR-1&217T, CVB3-34aT-3, and CVB3-34cT-3 proliferate and have oncolytic effects in various cancer cells and normal cells. As the cancer cells, the abovementioned NSCLC (H1299 cells) was used, and as the normal cells, the BEAS-2B cells were used.

Figure 11:
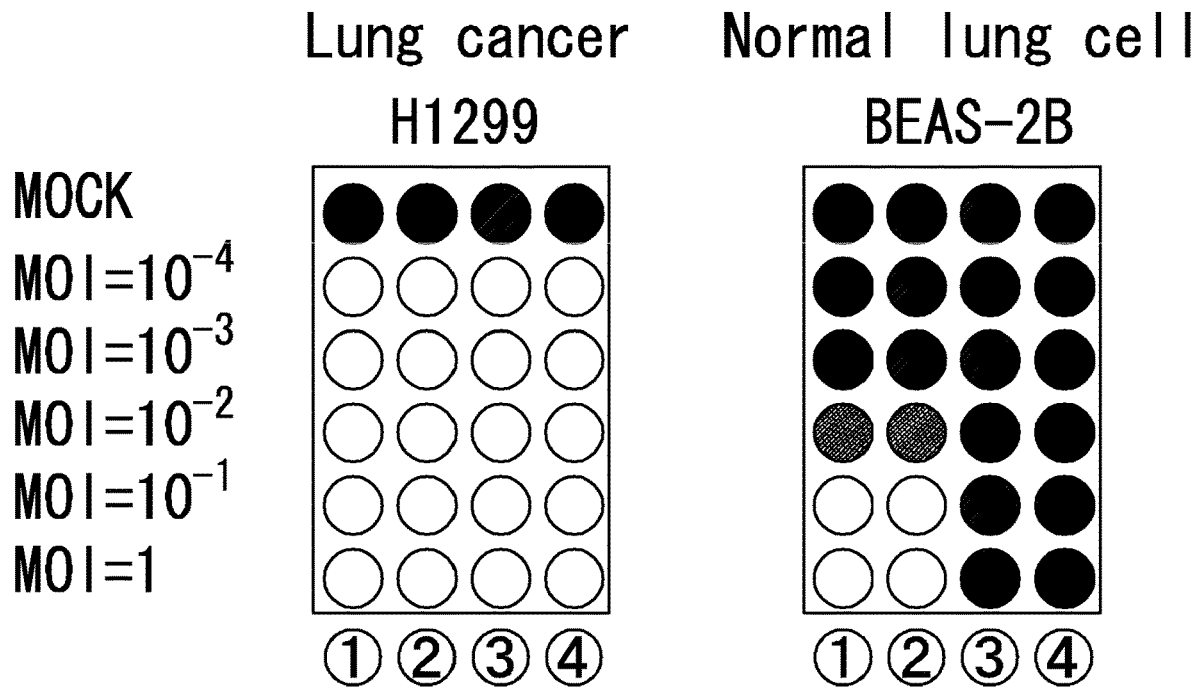
FIG. 11 is a schematic diagram showing whether or not CVB3-WT, CVB3-1&217T, CVB3-miR-34aT-3, and CVB3-miR-34cT-3 have oncolytic effects in cancer cells and normal cells.

Consequently, results indicating that the respective viruses exhibit sufficient oncolytic effects in the H1299 cells were obtained (see left diagram in FIG. 11). In the normal cells, oncolytic effects were confirmed for CVB3-WT and miR-1&217I respectively at a concentration of MOI=$10^{-2}$. On the other hand, with CVB3-34aT-3 and CVB3-34cT-3, oncolytic effects were not confirmed even with samples of the highest virus concentration (MOI=1) (see right diagram in FIG. 11).

From the above, it was made clear that CVB3-34aT-3 and CVB3-34cT-3 are capable of virus proliferation and exhibit oncolytic effects in the cancer cells. It was further made clear that, unlike miR-1&217T and CVB3-WT, CVB3-34aT-3 and CVB3-34cT-3 do not exhibit oncolytic effects and are suppressed in virus proliferation in the normal cells.

Figure 12:
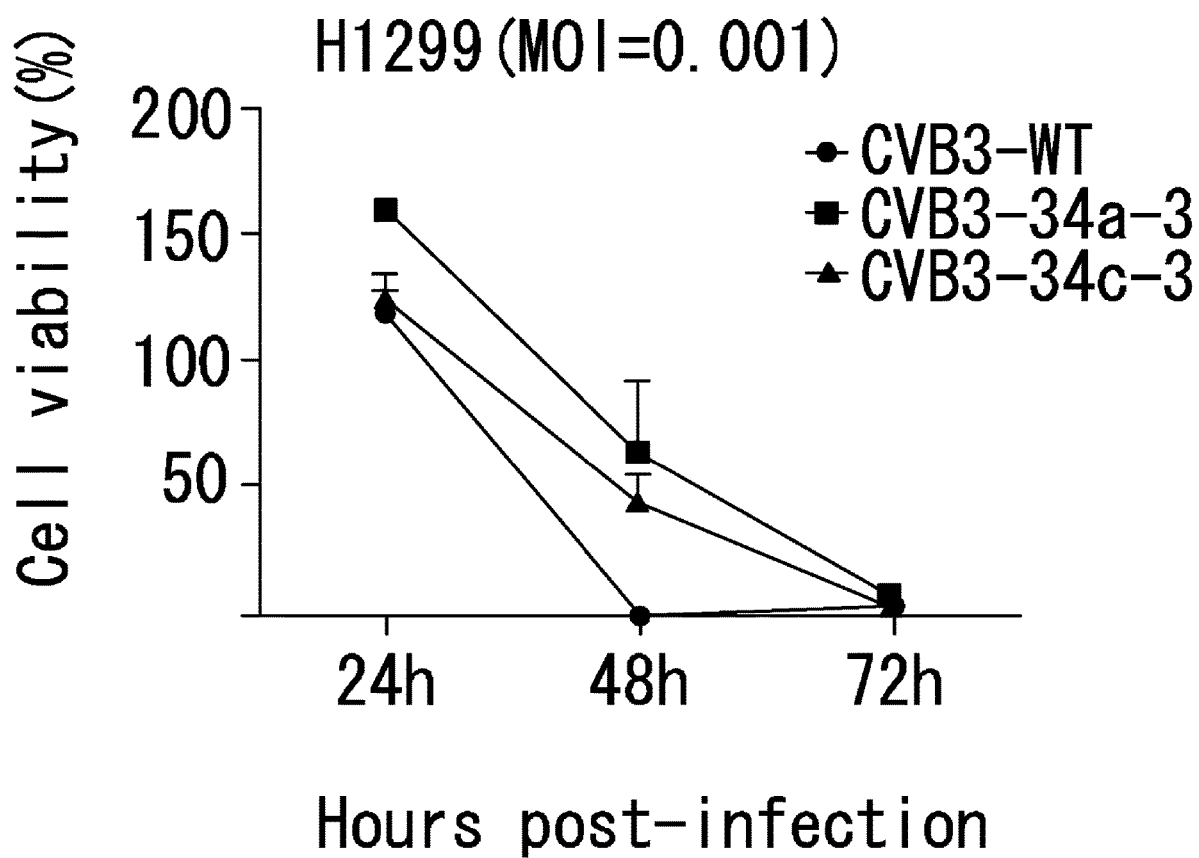
FIG. 12 is a graph of evaluation of cell viabilities of H1299 cells upon infection with CVB3-WT, CVB3-miR-34aT-3, and CVB3-miR-34cT-3 (MOI=0.001).
Figure 13:
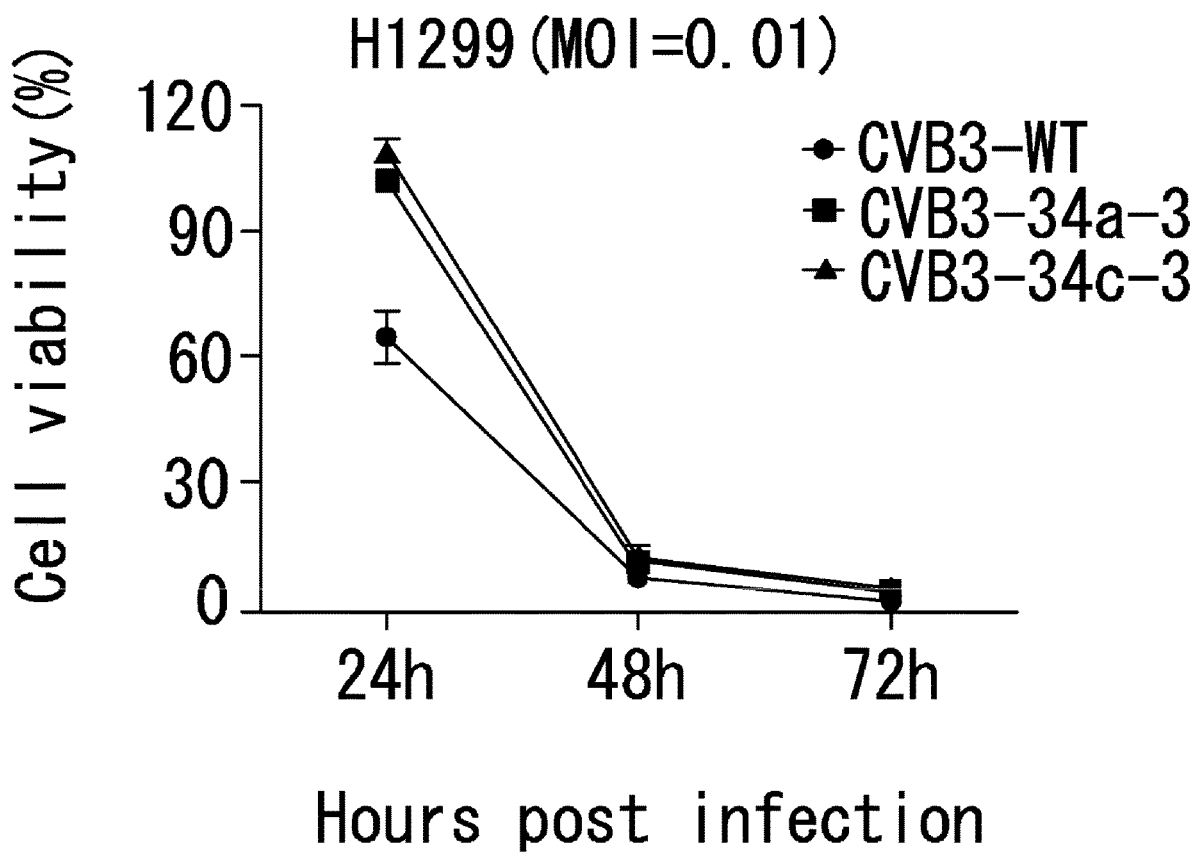
FIG. 13 is a graph of evaluation of cell viabilities of H1299 cells upon infection with CVB3-WT, CVB3-miR-34aT-3, and CVB3-miR-34cT-3 (MOI=0.01).

Next, cell viability tests of cancer cells and normal cells infected with the respective viruses of CVB3-WT, CVB3-34aT-3, and CVB3-34cT-3 were evaluated by an MTS method. Non-virus-infected H1299 cells ($1.0\times10^4$ cells) were infected with the respective viruses of CVB3-WT, CVB3-34aT-3, and CVB3-34cT-3 produced in H1299 cells and cell viabilities after 24 hours, after 48 hours, and after 72 hours were measured. In the test with MOI=0.001, the H1299 cells were substantially killed after 72 hours by all of CVB3-WT, CVB3-34aT-3, and CVB3-34cT-3 (see FIG. 12). Also, in the test with MOI=0.01, the H1299 cells were substantially killed after 72 hours by all of CVB3-WT, CVB3-34aT-3, and CVB3-34cT-3 (see FIG. 13).

Figure 14:
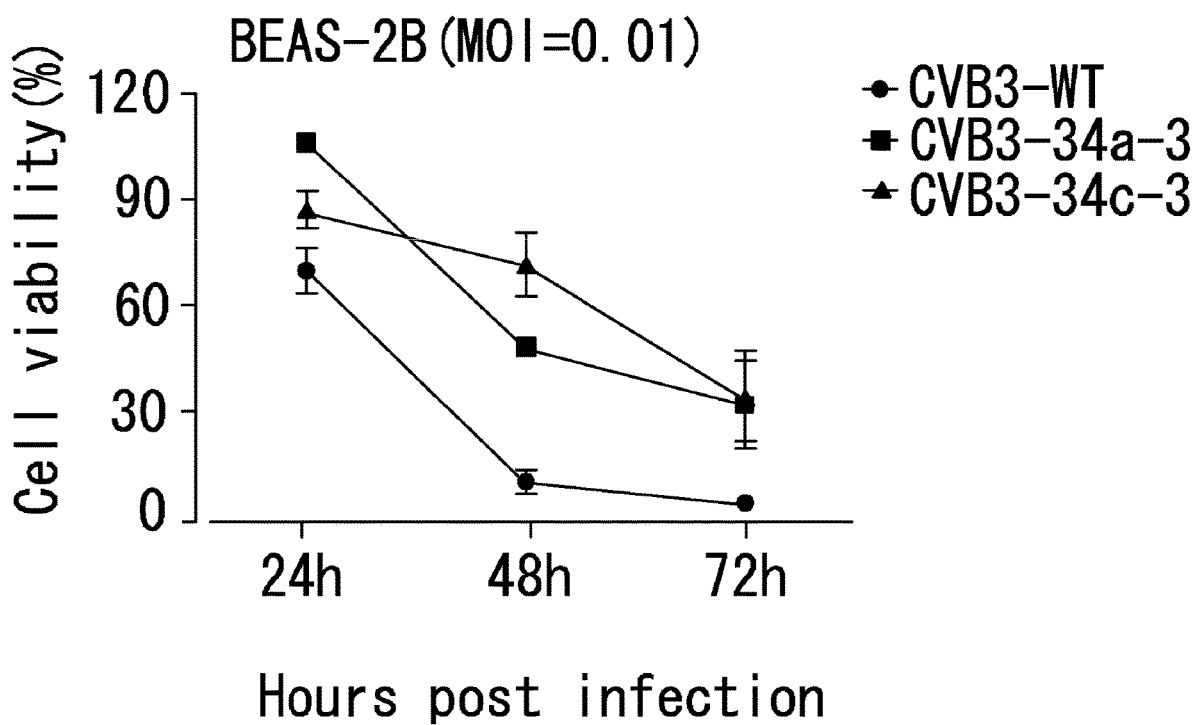
FIG. 14 is a graph of evaluation of cell viabilities of BEAS-2B cells upon infection with CVB3-WT, CVB3-miR-34aT-3, and CVB3-miR-34cT-3 (MOI=0.001).

Also, non-virus-infected BEAS-2B cells ($1.0\times10^4$ cells) were infected with the respective viruses of CVB3-WT, CVB3-34aT-3, and CVB3-34cT-3 produced in H1299 cells and the cell viabilities after 24 hours, after 48 hours, and after 72 hours were measured. In the test with MOI=0.01, whereas BEAS-2B cells were substantially killed after 72 hours by CVB3-WT, survival of the BEAS-2B cells after 72 hours was confirmed with CVB3-34aT-3 and CVB3-34cT-3 (see FIG. 14).

From the above, it was made clear that CVB3-34aT-3 and CVB3-34cT-3 are capable of virus proliferation and exhibit oncolytic effects in the cancer cells. It was also made clear that these viruses, unlike CVB3-WT, are suppressed in virus proliferation and strongly suppressed in cytotoxicity in the normal cells.

Figure 15:
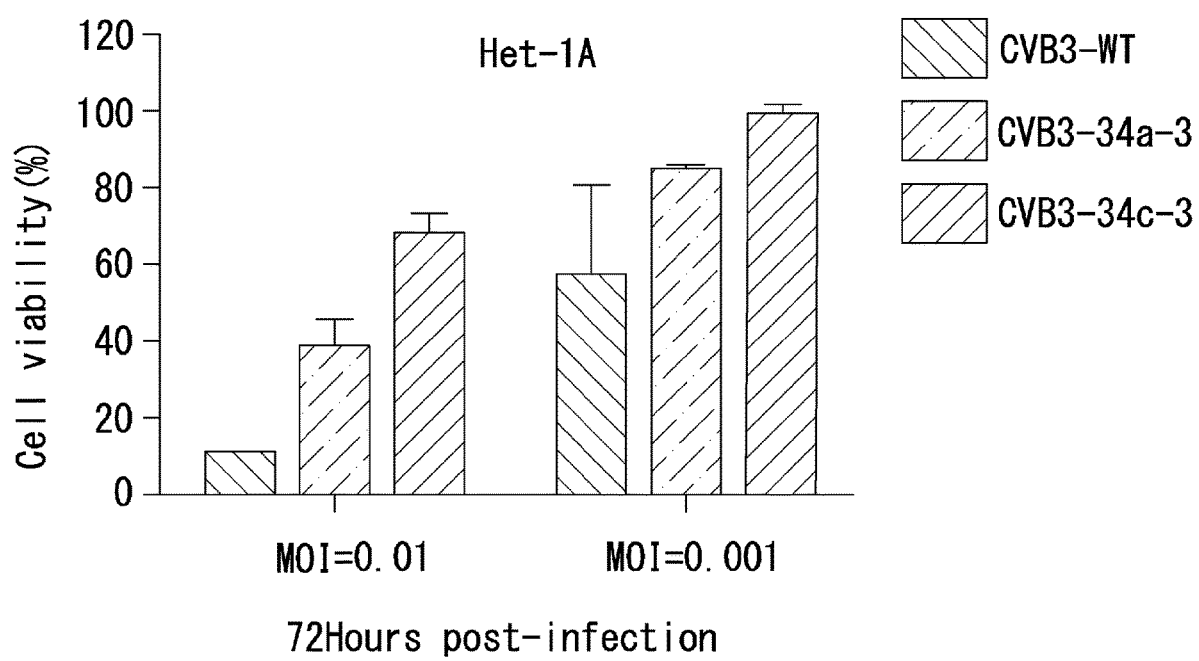
FIG. 15 is a graph of evaluation of cell viabilities after 72 hours of Het-1A cells upon infection with CVB3-WT, CVB3-miR-34aT-3, and CVB3-miR-34cT-3 (MOI=0.001 or MOI=0.01).
Figure 17:
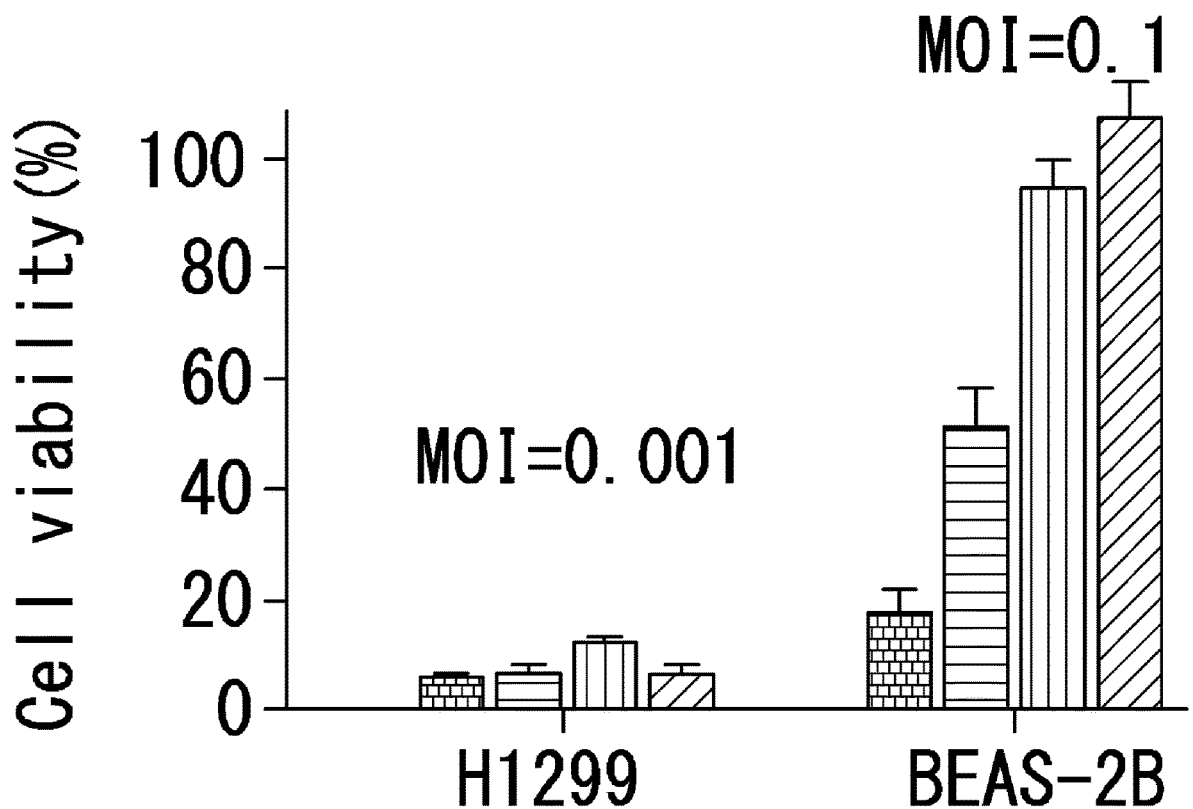
FIG. 17 is a graph of evaluation of cell viabilities after 72 hours of cancer cells (MOI=0.001) and normal cells (MOI=0.1) upon infection with CVB3-WT, CVB3-1&217T, CVB3-miR-34aT-3, and CVB3-miR-34cT-3.

Further, the cell viabilities after 72 hours of BEAS-2B cells ($1.0\times10^4$ cells) and Het-1A cells (($1.0\times10^4$ cells) are shown in FIG. 15.

As shown in FIG. 15, with MOI=0.001, and MOI=0.01, the cell viability of Het-1A cells was higher with CVB3-34aT-3 than with CVB3-WT, and CVB3-34cT-3 exhibited an even higher value than CVB3-34aT-3.

Figure 16:
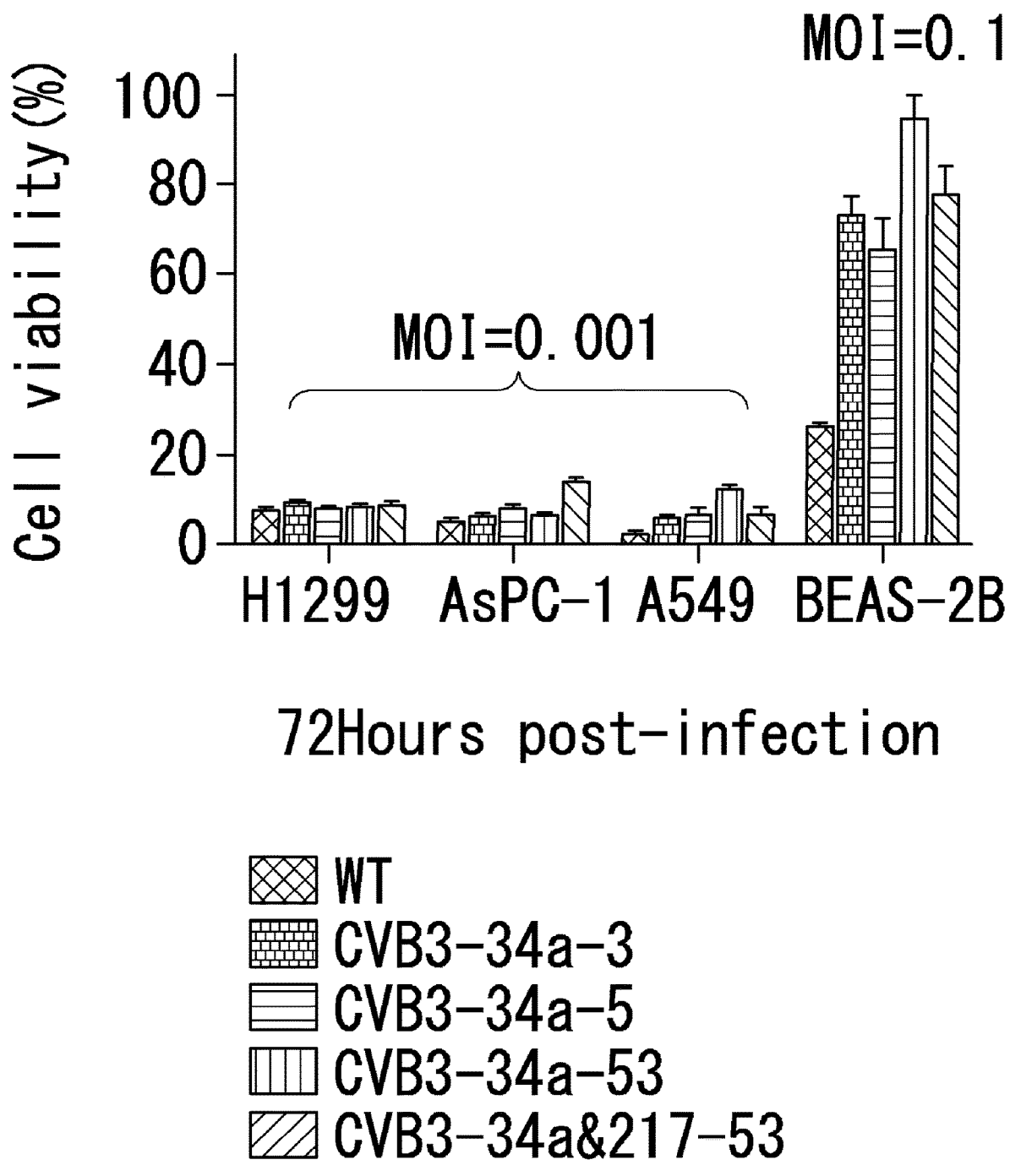

Next, the following FIG. 16 shows the results of evaluating cell viability tests of cancer cells and normal cells infected with the respective viruses of CVB3-WT, CVB3-34aT-3, CVB3-34aT-5, CVB3-34aT-53, and CVB3-34a&217T-53 (with MOI=0.001 for the cancer cells and MOI=0.1 for the normal cells) by the MTS method in the same manner as the above. For the tests shown in FIG. 16, cell viabilities after 72 hours determined by respectively using the lung cancer cell lines of NSCLC (A549 cells ($1.0\times10^4$ cells) and H1299 cells ($1.0\times10^4$ cells)) and the pancreatic cancer cell line of AsPC-1 cells ($1.0\times10^4$ cells) as the cancer cells and BEAS-2B cells ($1.0\times10^4$ cells) as the normal cells are shown.

As shown in FIG. 16, results where, in comparison to CVB3-WT, the cell viabilities of the BEAS-2B cells are higher with other respective viruses were exhibited. Also, results where the cell viabilities are higher with CVB3-34aT-53 and CVB3-34a&217T-53 in comparison to CVB3-34aT-3 and CVB3-34aT-5 were exhibited.

Next, the following FIG. 17 shows the results of evaluating cell viability tests of cancer cells and normal cells infected with the respective viruses of CVB3-WT, miR-1&217T, CVB3-34aT-3, and CVB3-34cT-3 (with MOI=0.001 for the cancer cells and MOI=0.1 for the normal cells) by the MTS method in the same manner as the above. For the tests shown in FIG. 17, cell viabilities after 72 hours determined by respectively using H1299 cells ($1.0\times10^4$ cells) as the cancer cells and BEAS-2B cells ($1.0\times10^4$ cells) as the normal cells are shown.

As shown in FIG. 17, results where, in comparison to CVB3-WT, the cell viabilities of the BEAS-2B cells are higher with other respective viruses were exhibited. Also, results where the cell viabilities are higher with CVB3-34aT-3 and CVB3-34cT-3 in comparison to miR-1&217T were exhibited.

I-3. Tumorigenesis Test Using Mice (In Vivo)

Next, mice were administered with a cancer cell line (H1299) to form tumors, the respective viruses of CVB3-WT, CVB3-34aT-3, and CVB3-34cT-3 were administered into the tumors, and changes in the tumors were observed. Although detailed test contents shall be described later, observation was performed over a fixed period and tumor volumes (see FIG. 18(a)), survival rates of the mice (see FIG. 18(b)), and body weights of the mice (see FIG. 19) were evaluated. At a point at which long diameters of the tumors of the mice reached 0.4 cm, the mice in treated groups were administered with the respective viruses every other day up to a maximum of five times (day 2, 4, 6, 8, and 10). Also, the mice in an untreated group were administered with Opti-MEM every other day up to a maximum of five times (day 2, 4, 6, 8, and 10). The study was performed with a sample number n=4 for each virus or control.

Figure 18:
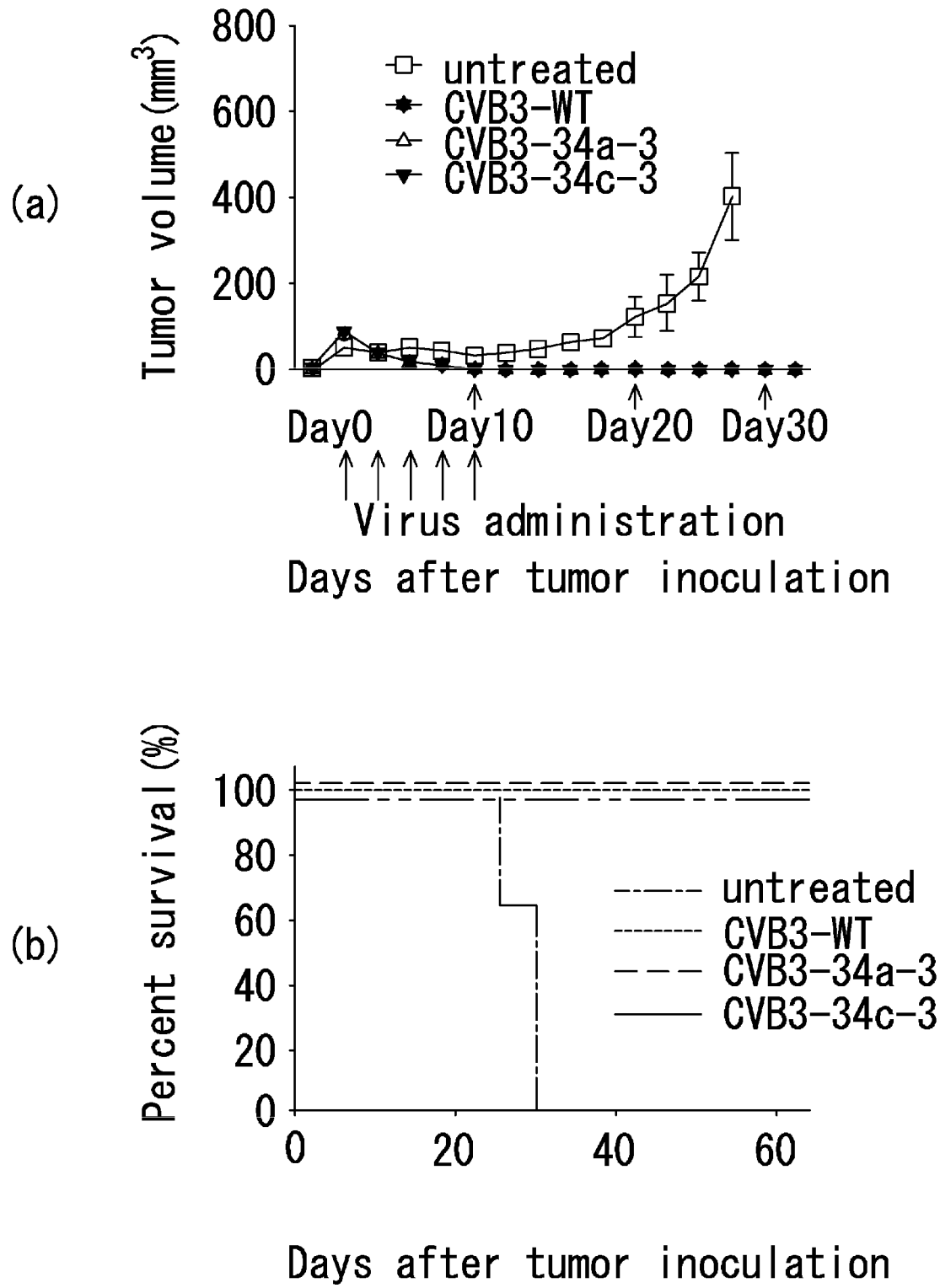
FIG. 18(a) is a graph showing changes with time in tumor volume (NCI-H1299) in mice of treated groups (CVB3-WT, CVB3-miR-34aT-3, and CVB3-miR-34cT-3) and an untreated group.
FIG. 18(b) is a graph showing survival rates of the same mice.

Consequently, the results that, with the mice of the untreated group (untreated), the tumor volume increases with time from the day of administration of the cancer cell line (H1299) were observed as shown in FIG. 18(a). On the other hand, the results for the mice of the treated groups administered with the respective viruses of CVB3-WT, CVB3-34aT-3, and CVB3-34cT-3 were that the tumor does not become larger and the tumor is not confirmed at the final stage. Also, as shown in FIG. 18(b), with the mice of the untreated group (untreated), the survival rate of the mice became 0% at approximately 30 days from the day of administration of the cancer cell line (H1299). On the other hand, with the mice of the treated groups administered with the respective viruses of CVB3-WT, CVB3-34aT-3, and CVB3-34cT-3, the survival rates were 100% even after elapse of approximately 60 days from the day of administration of the cancer cell line (H1299). The survival rates are calculated with the sample number of the mice being n=3 or 4.

Figure 19:
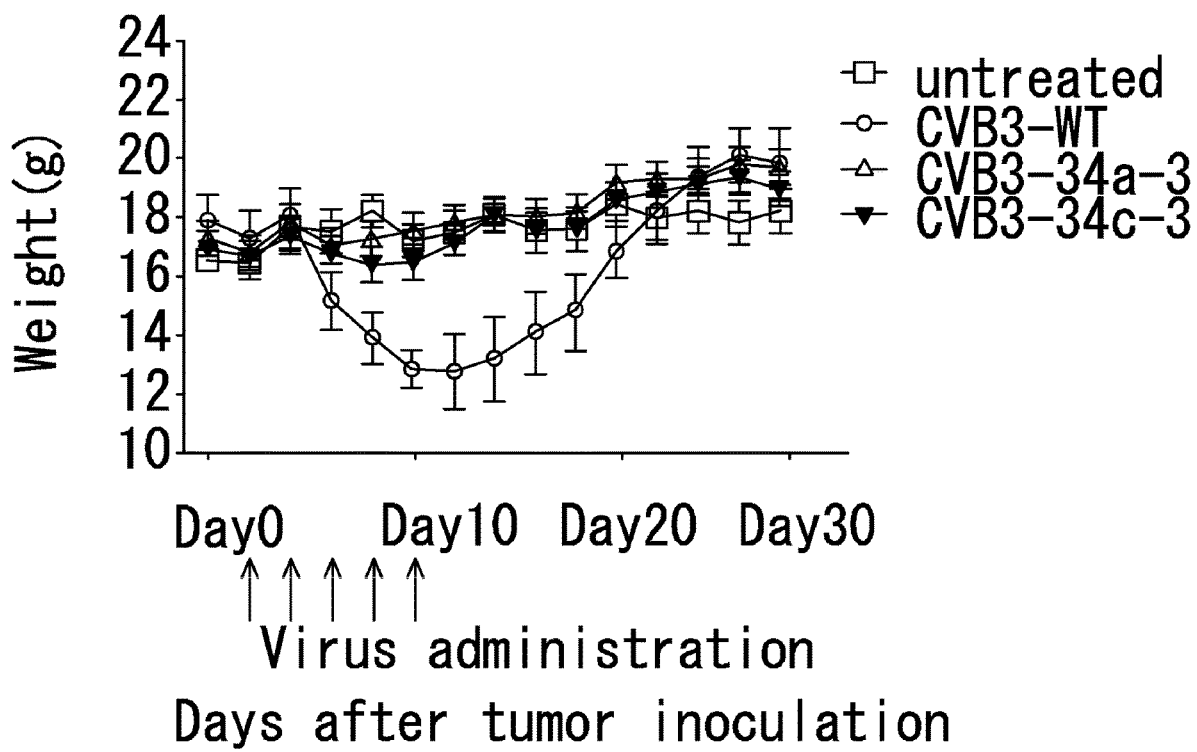
FIG. 19 is a graph showing changes in body weight of the mice of the treated groups (CVB3-WT, CVB3-miR-34aT-3, and CVB3-miR-34cT-3) and the untreated group.

Further, as shown in FIG. 19, in regard to changes in body weight of the mice, with the mice of the treated group administered with CVB3-WT, temporary decreases in body weight were observed at 10 days to 20 days from the day of administration of the cancer cell line (H1299). On the other hand, a decrease in body weight was not observed with the mice of the untreated group (untreated) and the mice of the treated groups administered with the respective viruses of CVB3-34aT-3 and CVB3-34cT-3. The decreases in body weight seen with the mice administered with CVB3-WT are presumed to have occurred due to an influence of a side effect caused by administration of CVB3-WT.

From the above results, it was made clear, even in the in vivo tests using mice, that the respective viruses of CVB3-34aT-3 and CVB3-34cT-3 exhibit the same oncolytic effects as CVB3-WT against a human lung cancer cell line (H1299). Also, a temporary decrease in body weight, which occurred with mice administered with CVB3-WT, did not occur with the mice administered with the respective viruses of CVB3-34aT-3 and CVB3-34cT-3, and the results thus suggested a possibility that the occurrence of a side effect is suppressed.

I-4. Blood Biochemical Examination Using Mice (In Vivo)

Next, mice were administered with a cancer cell line (H1299) to form tumors, and upon administering the respective viruses of CVB3-WT, CVB3-34a&217T-53, and miR-1&217T into the tumors, blood was sampled from mice of one-dose groups and mice of a two-dose groups of the respective viruses and a blood biochemical examination was performed. Although details shall be described later, in the blood biochemical examination, respective component amounts in blood of GOP/AST (liver and myocardium), LDH (liver, myocardium, and kidneys), GPT/ALT (liver and myocardium), and Amy (pancreas), which are markers of side effects caused by administration of CVB3-WT, were measured with a dry clinical chemical analyzer to evaluate whether or not there were side effects. With the mice of the one-dose group, the viruses were administered into the tumors on the second day from the day of administration of the cancer cell line (H1299) and blood was sampled from the mice two days later. Also, with the mice of the two-dose group, the viruses were administered into the tumors on the second day and the fourth day from the day of administration of the cancer cell line (H1299) and blood was sampled from the mice two more days later. The study was performed with a sample number n=3 or 4 for each virus or control.

Figure 20:
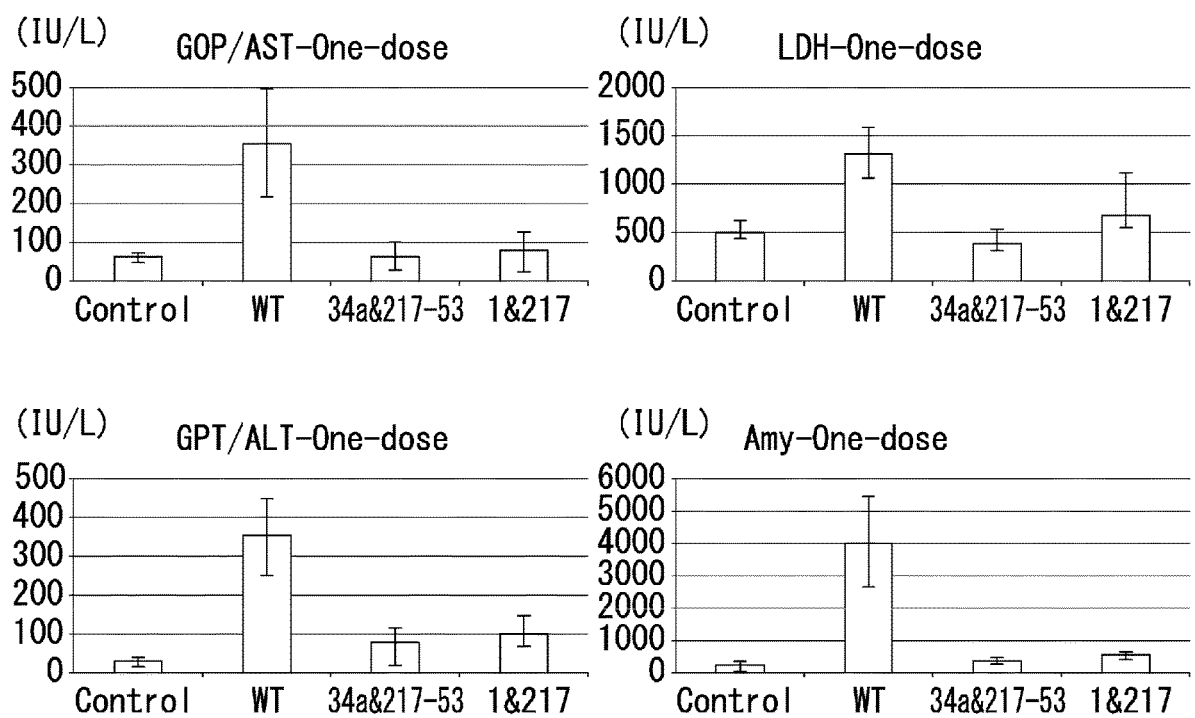
FIG. 20 shows graphs of results of blood biochemical examination of mice (one-dose groups) administered with CVB3-WT, CVB3-34a&217T-53, and CVB3-1&2171.
Figure 21:
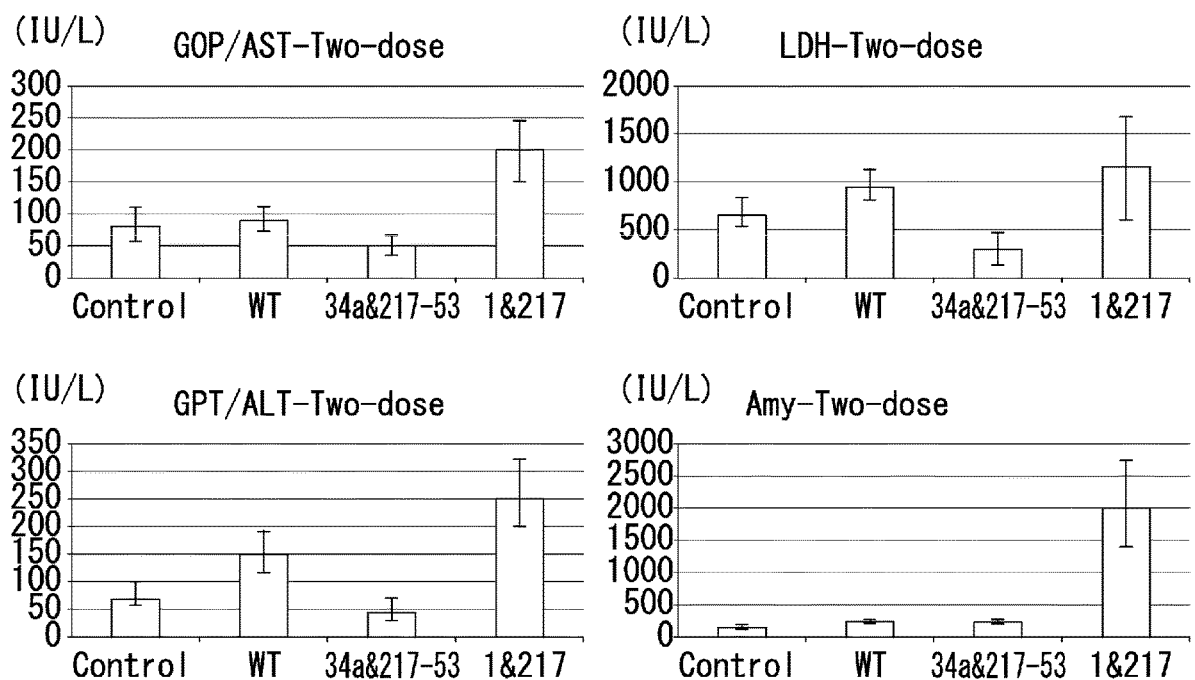
FIG. 21 shows graphs of results of blood biochemical examination of mice (two-dose groups) administered with CVB3-WT, CVB3-34a&217T-53, and CVB3-1&2171.

Consequently, as shown in FIG. 20, with the one-dose group, the component amounts of the respective markers were detected highly and side effects occurred in the mice administered with CVB3-WT. On the other hand, component amounts of approximately the same levels as the control were detected in the mice administered with the respective viruses of CVB3-34a&217T-53 and miR-1&217T. Also, as shown in FIG. 21, with the two-dose group, the component amounts of the respective markers were detected most highly in the mice administered with miR-1&217T. On the other hand, with the mice administered with CVB3-34a&217T-53, results indicated component amounts of approximately the same levels as or not more than the control. In addition, in regard to the component amounts being not so highly detected with the mice administered with CVB3-WT in the two-dose group, it is presumed that the component amounts of the respective markers increased already at the timing of the first dose and thereafter decreased.

Figure 22:
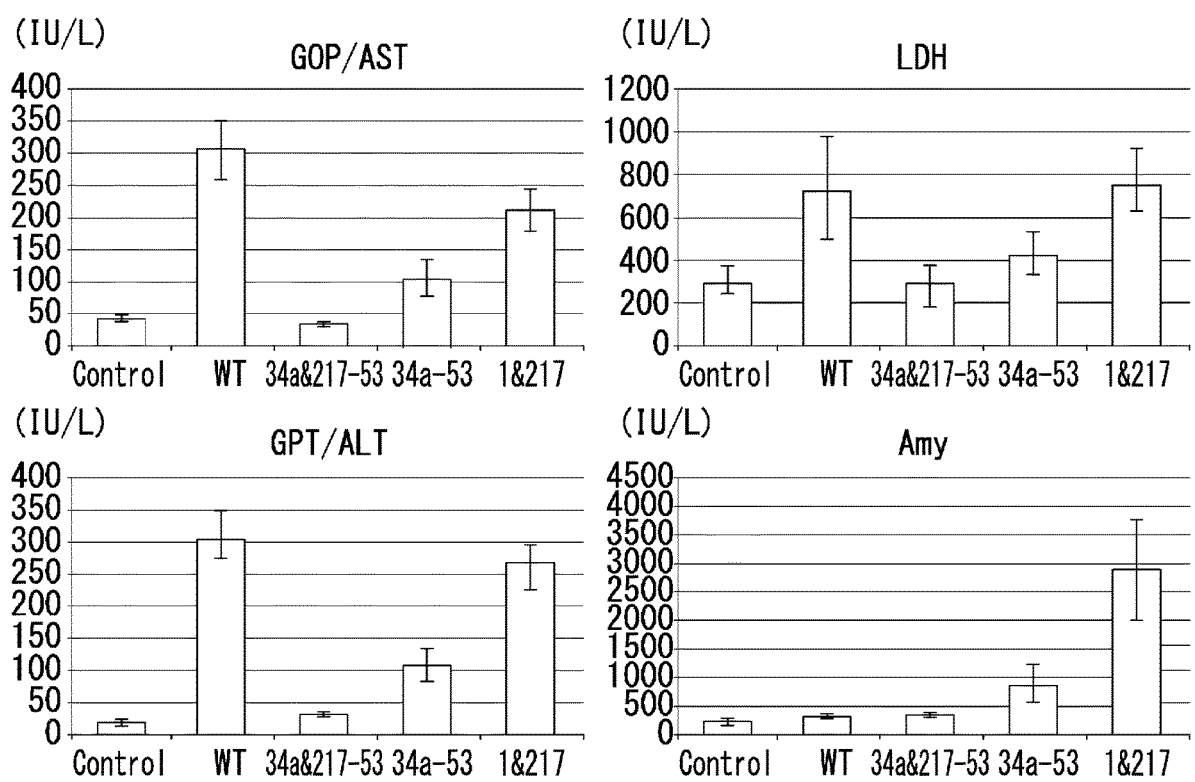
FIG. 22 shows graphs of results of blood biochemical examination of mice (two-dose groups) administered with CVB3-WT, CVB3-34a&217T-53, CVB3-miR-34aT-53, and CVB3-1&2171.

Also, FIG. 22 shows results of mice of two-dose groups with which the respective viruses of CVB3-WT, CVB3-34a&217T-53, CVB3-34aT-53, and miR-1&217T were administered into the tumors. Consequently, the component amounts of the respective markers were detected highly and side effects occurred in the mice administered with CVB3-WT and miR-1&217T. On the other hand, with the mice administered with CVB3-34aT-53, the results were such that, although higher component amounts of the respective markers were detected than the control, the component amounts of the respective markers were lower than those of CVB3-WT and miR-1&217T and it was thus confirmed that side effects were more suppressed than these viruses. Further, with the mice administered with CVB3-34a&217T-53, component amounts of the respective markers of approximately the same levels as or not more than the control were indicated.

The above results show that, in the blood biochemical examination using mice, the occurrence of side effects, which occurred in the mice administered with CVB3-WT, was suppressed in the mice administered with CVB3-34a&217T-53 and CVB3-34aT-53. Also, comparing CVB3-34a&217T-53 and miR-1&217T, it was made clear that CVB3-34a&217T-53 is more likely to suppress the occurrence of side effects. Further, comparing CVB3-34a&217T-53 and CVB3-34aT-53, it was made clear that CVB3-34a&217T-53 is even more likely to suppress the occurrence of side effects.

I-5. Comparison of 5' UTR and 3' UTR as Insertion Positions for Target Sequences Next, respective target sequences were inserted in the 5' UTR (between the positions 742 and 743 bp) and the 3' UTR (between the positions 7304 and 7305 bp) and target-sequence-inserted viruses were subcultured three times or six times to confirm whether or not the target sequences became detached from the genome and evaluate retention stabilities of the target sequences. A base length of the CVB3 genome is approximately 400 bp and a base length with the respective target sequences inserted in the CVB3 genome is approximately 500 bp. The CVB3 genomes extracted from respective samples were electrophoresed by a known electrophoresis method and the base lengths were confirmed. That is, if detachment of the target sequences from the CVB genome occurred, the base length is confirmed to be approximately 400 bp.

Figure 23:
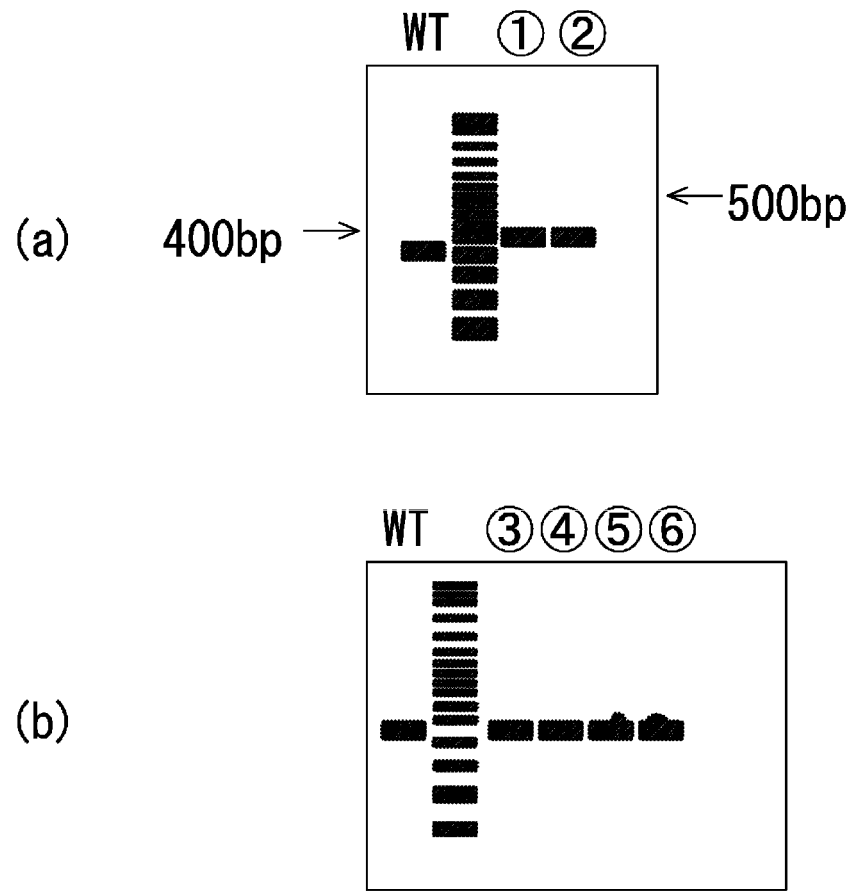
FIG. 23 shows schematic diagrams of results of electrophoresis of PCR products of vicinities of target sites in a CVB3 genome and in a CVB3 genome inserted with target sequences.

Electrophoresis results of electrophoresing products obtained using a genome extracted from CVB3-WT that is not inserted with any target sequence and genomes extracted from CVB3-34aT-3 and CVB3-34cT-3 that were subcultured three times and amplifying vicinities of the target sequence insertion sites by a PCR reaction are schematically shown in FIG. 23(a). Also, electrophoresis results of electrophoresing products obtained using a genome extracted from CVB3-WT that is not inserted with any target sequence, genomes extracted from CVB3-34aT-3 and CVB3-34cT-3 that were subcultured six times, and genomes extracted from CVB3-34aT-3 and CVB3-34cT-3 that were subcultured ten times and amplifying the vicinities of the target sequence insertion sites by the PCR reaction are schematically shown in FIG. 23 (b). That is, FIG. 23(a) and FIG. 23(b) show results of inserting the target sequences in 3' UTR and subculturing the respective viruses.

Figure 24:
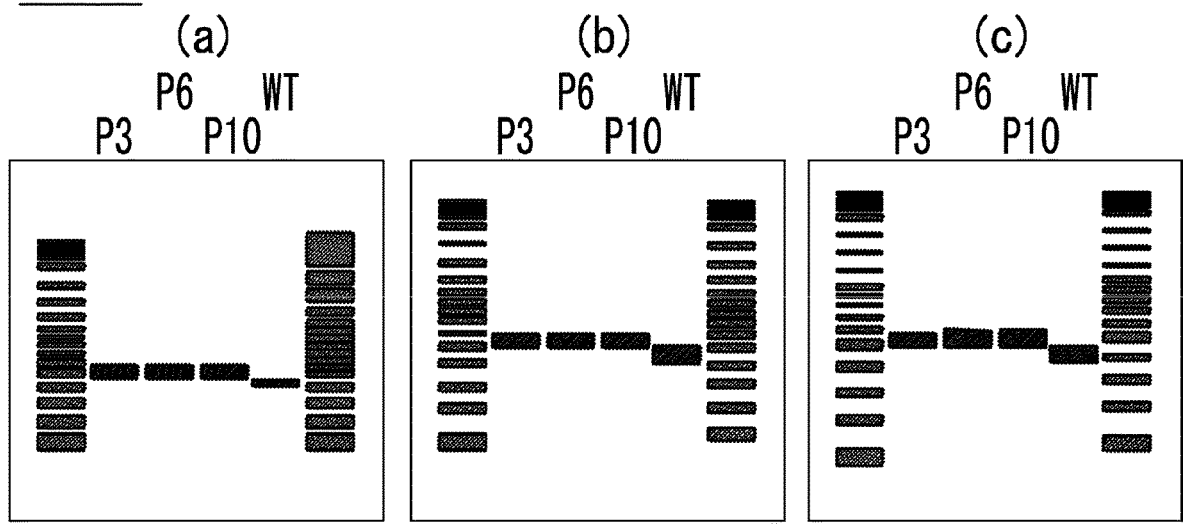
FIG. 24 shows schematic diagrams of results of electrophoresis of PCR products of vicinities of target sites in a CVB3 genome and in a CVB3 genome inserted with target sequences.
Figure 24:
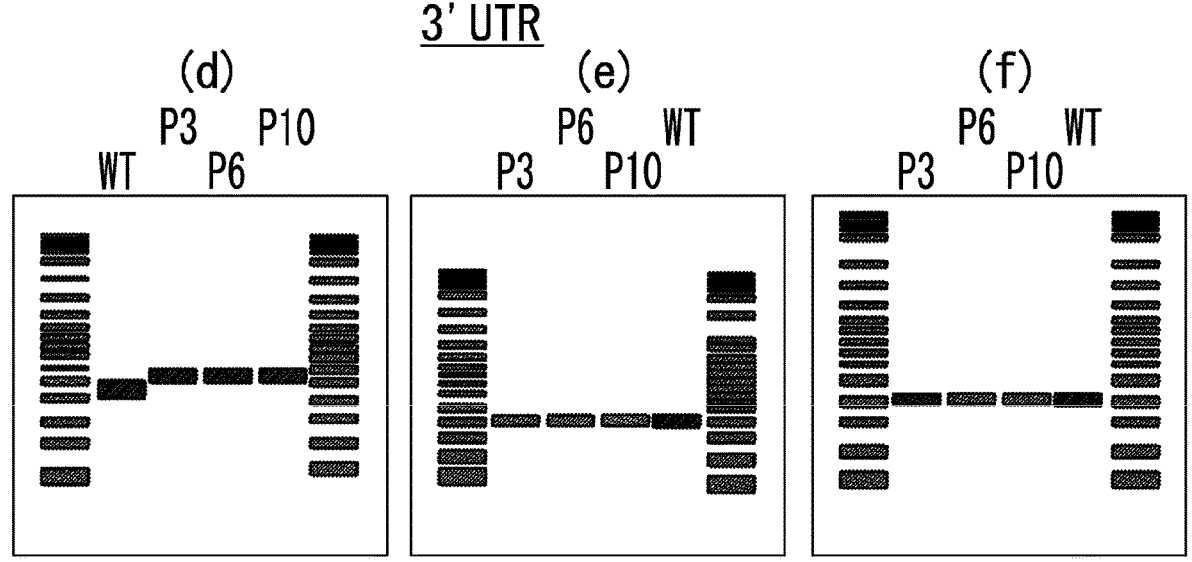

Also, electrophoresis results of electrophoresing products obtained using genomes extracted from CVB3-WT that is not inserted with any target sequence and genomes extracted from viruses that were inserted with the respective target sequences and were subcultured three, six, and ten times and amplifying vicinities of the target sequence insertion sites by the PCR reaction are schematically shown in FIG. 24 (a) to FIG. 24(f). FIG. 24 (a) shows the results of the PCR reaction of the vicinity of the target sequences inserted in the 5' UTR in the CVB3-34aT-53 virus genome. FIG. 24(b) shows the results of the PCR reaction of the vicinity of the target sequences inserted in the 5' UTR in the CVB3-34a&217T-53 virus genome. FIG. 24(c) shows the results of the PCR reaction of the vicinity of the target sequences inserted in the 5' UTR in the CVB3-34aT-5 virus genome. FIG. 24(d) shows the results of the PCR reaction of the vicinity of the target sequences inserted in the 5' UTR in the CVB3-34cT-5 virus genome. FIG. 24 (e) shows the results of the PCR reaction of the vicinity of the target sequences inserted in the 3' UTR in the CVB3-34aT-53 virus genome. FIG. 24(f) shows the results of the PCR reaction of the vicinity of the target sequences inserted in the 3' UTR in the CVB3-34a&217T-53 virus genome. That is, FIG. 24(a) to FIG. 24(d) show results of subculturing the respective viruses with the target sequences inserted in the 5' UTR. Also, FIG. 24 (e) and FIG. 24 (f) show results of subculturing the respective viruses with the target sequences inserted in the 3' UTR.

Consequently, it was made clear from FIG. 23(a) and FIG. 23(b) that, with CVB3-34aT-3 and CVB3-34cT-3, whereas the target sequences are retained on the genomes at the point of being subcultured three times, the target sequences are detached from being on the genomes at the point of being subcultured six times or ten times.

Also, from FIG. 24 (a) to FIG. 24 (d), it was made clear that, with the viruses with the respective target sequences inserted in the 5' UTR, the target sequences are retained on the genomes without becoming detached even at the points of being cultured three times, six times, and ten times. Further, from FIG. 24 (e) and FIG. 24 (f), it was made clear that, with the viruses with the respective target sequences inserted in the 3' UTR, the target sequences are detached from being on the genomes at the point of being subcultured three times, six times or ten times. From the above results, it was made clear that, as the position on the CVB3 genome for inserting a target sequence for miRNA, the 5' UTR (between the positions 742 and 743 bp) can more stably retain the target sequence than the 3' UTR (between the positions 7304 and 7305 bp).

I-6. Methods Summary

The present study was carried out in accordance with the following protocols.

[Preparation of Respective Gene-Modified Viruses]

<Names of Prepared Viruses>

CVB3-34aT-3

CVB3-34cT-3

CVB3-34aT-5

CVB3-34cT-5

CVB3-34aT-53

CVB3-34a&217T-53 miR-1&217T

<Vector Construction>

(Materials & Reagents)

CVB3 Plasmid

KOD—Plus-neo

UltraPure

Primer (CVB3-miR-34aT)

miR-34aT-Inverse Forward
(SEQ ID NO: 9)
AACCAGCTAAGACACTGCCAGAGACAATTTGAAATAATTTAGATTGG (10 pmol/μl)

miR-34aT-Inverse Reverse
(SEQ ID NO: 10)
GCAGTGTCTTAGCTGGTTGTTAATCTAAAAGGAGTCCAACC (10 pmol/μl)

miR-34aT × 4+
(SEQ ID NO: 3)
ACAACCAGCTAAGACACTGCCAcgatACAACCAGCTAAGACACTGCCAa ccggtACAACCAGCTAAGACACTGCCAtcacACAACCAGCTAAGACACT GCCA (1 umol/μl)

miR-34aT × 4-
(SEQ ID NO: 11)
TGGCAGTGTCTTAGCTGGTTGTgtgaTGGCAGTGTCTTAGCTGGTTGTa ccggtTGGCAGTGTCTTAGCTGGTTGTatcgTGGCAGTGTCTTAGCTGG TTGT (1 umol/μl)

Primer (CVB3-miR34cT)

miR-34cT-Inverse Forward
(SEQ ID NO: 12)
ATCAGCTAACTACACTGCCTGAGACAATTTGAAATAATTTAGATTGG
(10 pmol/μl)

miR-34cT-Inverse Reverse
(SEQ ID NO: 13)
CAGTGTAGTTAGCTGATTGCTAATCTAAAAGGAGTCCAACC (10 pmol/μl)

miR-34cT × 4+
(SEQ ID NO: 4)
GCAATCAGCTAACTACACTGCCTcgatGCAATCAGCTAACTACACTGCC
TaccggtGCAATCAGCTAACTACACTGCCTtcacGCAATCAGCTAACTA
CACTGCCT (10 umol/μl)

miR-34cT × 4−
(SEQ ID NO: 14)
AGGCAGTGTAGTTAGCTGATTGCgtgaAGGCAGTGTAGTTAGCTGATTG
CaccggtAGGCAGTGTAGTTAGCTGATTGCatcgAGGCAGTGTAGTTAG
CTGATTGC (10 umol/μl)

CVB3-34a-5-Reverse
(SEQ ID NO: 15)
GCAGTGTCTTAGCTGGTTGTTTTGCTGTATTCAACTTAACAATG
(10 pmol/μl)

CVB3-34a-5-Forward
(SEQ ID NO: 16)
AACCAGCTAAGACACTGCCAATGGGAGCTCAAGTATCAAC (10 pmol/μl)

CVB3-34c-5-Reverse
(SEQ ID NO: 17)
GCTTTGCTGTATTCAACTTAACAATGAATTG (10 pmol/μl)

CVB3-34c-5-Forward
(SEQ ID NO: 18)
ATGGGAGCTCAAGTATCAAC (10 pmol/μl)

CVB3-in-34c-5+
(SEQ ID NO: 19)
GTTGAATACAGCAAAGCAATCAGCTAACTACACTGCCTCGATGCAATCA
GCTAACTACACTGCCTACCGGTGCAATCAGCTAACTACACTGCCTTCAC
GCAATCAGCTAACTACACTGCCTATGGGAGCTCAAGTA (1 μmol/μl)

CVB3-in-34c-5−
(SEQ ID NO: 20)
TACTTGAGCTCCCATAGGCAGTGTAGTTAGCTGATTGCGTGAAGGCAGT
GTAGTTAGCTGATTGCACCGGTAGGCAGTGTAGTTAGCTGATTGCATCG
AGGCAGTGTAGTTAGCTGATTGCTTTGCTGTATTCAAC (1 μmol/μl)

CVB3-34a&217-5-Reverse
(SEQ ID NO: 21)
GCAGTGTCTTAGCTGGTTGTTTTGCTGTATTCAACTTAACAATG
(10 pmol/μl)

CVB3-34a&217-5-Forward
(SEQ ID NO: 22)
AATCAGTTCCTGATGCAGTAATGGGAGCTCAAGTATCAACGC
(10 pmol/μl)

CVB3-34a&217-3-Reverse
(SEQ ID NO: 23)
GCAGTGTCTTAGCTGGTTGTTAATCTAAAAGGAGTCCAACCACTTC
(10 pmol/μl)

CVB3-34a&217-3-Forward
(SEQ ID NO: 24)
AATCAGTTCCTGATGCAGTAGAGACAATTTGAAATAATTTAGATTG
(10 pmol/μl)

miR-34a × 2 & miR-217 × 2+
(SEQ ID NO: 25)
ACAACCAGCTAAGACACTGCCACGATACAACCAGCTAAGACACTGCCAA
CCGGTTCCAATCAGTTCCTGATGCAGTATCACTCCAATCAGTTCCTGAT
GCAGTA (1 μmol/μl)

miR-34a × 2 & miR-217 × 2−
(SEQ ID NO: 26)
TACTGCATCAGGAACTGATTGGAGTGATACTGCATCAGGAACTGATTGG
AACCGGTTGGCAGTGTCTTAGCTGGTTGTATCGTGGCAGTGTCTTAGCT
GGTTGT (1 μmol/μl)

CVB3-miR-Forward
(SEQ ID NO: 27)
CAGGTCTTTGAGGGGAACAA (20 pmol/μl)

CVB3-miR-Reverse
(SEQ ID NO: 28)
ATTAATGCAGCTGGCACGAC (20 pmol/μl)

miR-1&217T Forward
(SEQ ID NO: 29)
ttaATACATACTTCTTTACATTCCAcgatATACATACTTCTTTACATTC
CAaccggtTCCAATCAGTTCCTGATGCAGTAtcacTCCAATCAGTTCCT
GATGCAGTAgagacaatttgaaataatttag (20 pmol/μl)

miR-1&217T Reverse
(SEQ ID NO: 30)
ctcTACTGCATCAGGAACTGATTGGAgtgaTACTGCATCAGGAACTGAT
TGGAaccggtTGGAATGTAAAGAAGTATGTATatcgTGGAATGTAAAGA
AGTATGTATtaatctaaaaggagtccaacca (20 pmol/μl)

(Methods)
1. Mix the following reagents in the following order in a 0.2 ml PCR tube on ice.

TABLE 2

| Reagent | miR-34aT | miR-34cT |
|---|---|---|
| UltraPure | 33 μl | 33 μl |
| 10× Buffer for KOD -Plus- | 5 μl | 5 μl |
| 2 mM dNTPs | 5 μl | 5 μl |
| 25 mM MgSO$_4$ | 3 μl | 3 μl |
| Plasmid | 1 μl | 1 μl |
| Primer Forward | SEQ ID NO: 9 (1 μl) | SEQ ID NO: 12 (1 μl) |
| Primer Reverse | SEQ ID NO: 10 (1 μl) | SEQ ID NO: 13 (1 μl) |
| KOD -Plus- Neo | 1 μl | 1 μl |

2. Stir by tapping or gentle pipetting, spin down lightly, and collect the solution. Execute the following program with a thermal cycler made by Eppendorf AG.
3. (1) miR-34aT: 94° C. 2:00, 98° C. 0:10, 60° C. 0:30, 68° C. 6:30 (28 cycles), 72° C. 7:00
(2) miR-34cT: 94° C. 2:00, 98° C. 0:10, 57° C. 0:30, 68° C. 6:30 (28 cycles), 72° C. 7:00

4. Purify the PCR products and perform restriction enzyme treatment with Dpn I for 1 hour.
5. Perform agarose gel electrophoresis using the restriction enzyme treatment products and cut out the target bands.
6. Prepare double-strand inserts. Place 1 μl each of SEQ ID NOS: 3 and 11 or SEQ ID NOS: 4 and 14 in a tube, heat in annealing buffer at 94° C. for 10:00, cool to 25° C. at −1° C./1 min, and let react at 25° C. for 5:00.
7. After gel purification and then after restriction enzyme treatment, use In-fusion to let CVB3 plasmid (150 ng) and the double-strand insert (60 ng) react at 50° C. for 15 min.
8. Introduce the In-fusion product into competent cells and culture at 37° C.
9. On the next day, pick up the colonies and culture in an LB medium.
10. Recover the plasmid from the culture and check whether or not the miRNA target sequences have been inserted.

<Virus RNA Preparation>
(Materials & Reagents)
MEGAscript (registered trademark) KitAmbion Cat #AM1333*Store at −20° C.
CVB3 plasmid (CVB3-WT, CVB3-miR-1&217T, and CVB3-miR-217T)
Phenol:Chloroform 5:1, Acid-equilibrated: pH 4.7 Sigma Cat #P1944-100ML Lot #010M1574
Chloroformnacalai tesque Cat #08402-55 Lot #V6K0595
75% Ethanol (use nuclease-free water)
10 mol/l-Ammonium Acetate Solution nacalaitesqueCat #02432-74 Lot #L2B2291
UltraPure (Methods)

1. Mix the following reagents in the following order in a 0.2 ml PCR tube at room temperature (total: 20 µl).

TABLE 3

| Reagent | Volume |
|---|---|
| Linear template DNA (0.1-1 µg) | x µl |
| Nuclease-free Water | (8 − x) µl |
| ATP solution | 2 µl |
| CTP solution | 2 µl |
| GTP solution | 2 µl |
| UTP solution | 2 µl |
| 10× Reaction Buffer | 2 µl |
| Enzyme Mix | 2 µl |
| Total | 20 µl |

2. Let react at 37° C. for 3 h in a thermal cycler (use thermal cycler made by Bio-Rad Inc.).
3. After 3 h, add 1 µl of TURBO DNase into the tube in reaction, stir well, and let react additionally at 37° C. for 15 min.
4. Prepare in advance 1.1 times the number of reaction tubes of solutions, with each of which 114 µl of UltraPure and 15 µl of the accessory Ammonium Acetate Stop Solution are mixed in a 1.5 ml tube.
5. After the reaction, add 129 µl of the abovementioned mixed solution into the reaction tube and then perform pipetting.
6. Transfer the entire amount into a 0.7 ml tube.
7. Add 150 µl of Phenol:Chloroform thereto and then perform pipetting and mixing by inverting.
8. Centrifuge at 10,000×g for 2 min at room temperature.
9. Transfer the supernatant (approx. 150 µl) into a separate, new 0.7 ml tube.
10. Add 150 µl of Chloroform to the aqueous layer and then mix by inverting.
21. Centrifuge at 10,000×g for 2 min at room temperature.
22. Transfer the supernatant (approx. 100 µl) into a separate, new 0.7 ml tube.
23. Add 150 µl of cold 5M Ammonium acetate to the aqueous layer and then perform pipetting.
24. Leave to stand on ice for 10 min.
25. Centrifuge at 10,000×g for 15 min at 4° C.
26. Use a Pipetman to slowly remove the supernatant.
27. Gently add 200 µl of 75% Ethanol.
28. Centrifuge at 10,000×g for 15 min at 4° C.
29. Use a Pipetman to slowly remove the supernatant as much as possible.
30. Add 70 µl of UltraPure to the pellet and dissolve.

<Virus Preparation>

(Materials & Reagents)

NCI-H1299 cells ($1\times10^7$ cells/30 ml/dish)
RPMI 1640 w/10% FBS (growth medium)
Opti-MEM (registered trademark) I
Lipofectamine™ 2000 Reagent Invitrogen Cat #11668-019
In vitro transcription product (Methods)

1. To dispensed Opti-MEM, add RNA to 80 µg into the liquid, and to Opti-MEM dispensed in a separate tube, add 120 µl of Lipofectamine 2000 into the liquid.
2. Let both stand for 5 min at room temperature.
3. Mix both tubes and let stand for 20 min at room temperature.
4. After 20 min, add the entire amount of the mixed solution to NCI-H1299 cells.
5. After 4 h, replace with growth medium.
6. Incubate at 37° C. under 5% $CO_2$ for 24 h.
7. After 25 h from transfection, use a cell scraper to peel off the respective NCI-H1299 cells without discarding the medium.
8. Recover the supernatant, together with the cells, into a 50 ml tube.
9. Immerse the 50 ml tube in liquid $N_2$ to freeze.
10. Thaw with a water bath at 37° C.
11. Repeat the freezing and thawing of 9 and 10 two times (freezing and thawing are performed a total of three times).
12. Centrifuge at 3,000 rpm for 15 min at 4° C.
13. Replace the NCI-H1299 cell medium onto which the supernatant is to be transferred with fresh medium (15 ml).
14. Add the entire amount of the supernatant after centrifugation to the NCI-H1299 cells.
15. Incubate at 37° C. under 5% $CO_2$ for 6 to 8 h.
16. When CPE is confirmed in 60 to 70% or more, remove the culture supernatant.
17. Add 2 ml of Opti-MEM (registered trademark) I.
18. Peel off the cells with a cell scraper.
19. Recover the entire amount of Opti-MEM (registered trademark) I together with the cells into a 15 ml tube.
20. Immerse this 15 ml tube in liquid nitrogen and freeze (approx. 2 min).
21. Thaw with a water bath at 37° C. (approx. 10 min).
22. Repeat the freezing and thawing of 20 and 21 two times (freezing and thawing are performed a total of three times).

23. Centrifuge at 3,000 rpm for 15 min at 4° C.
24. Preserve the supernatant at −80° C.

<Virus Titer Measurement>
(Materials & Reagents)
96 well plate (flat bottom)
NCI-H1299 cells ($5×10^3$ cells/100 μl/well)
RPMI 1640 w/10% FBS (growth medium)
96 well plate (round bottom)
Opti-MEM (registered trademark) I
(Methods)
1. Inoculate the NCI-H1299 cells into all wells of the 96 well Flat plate at $5×10^3$ cells/100 μl/well.
2. Incubate at 37° C. under 5% $CO_2$ for 7 h.
3. Add 180 μl of Opti-MEM to each well from the second column to the last, twelfth column of the 96 well Round plate.
4. For the first column that is the highest virus concentration column (ordinarily $10^{-2}$), add 990 μl of Opti-MEM into a 1.5 ml tube, add 10 μl of the virus stock solution thereto, and perform adequate pipetting to prepare the $10^2$ solution.
5. Add 120 μl of the virus $10^{-2}$ column solution to each well of the first column of the 96 well Round plate.
6. Use an 8-channel electronic pipette to transfer 20 μl of the first column virus solution to each well of the second column.
7. Perform pipetting once at this point and then change the tip.
8. Take 20 μl from each well of the column diluted immediately before and transfer to each well of the adjacent column.
9. Perform pipetting once and then change the tip.
10. Repeat 8. and 9. until the eleventh column.
11. Take out the Flat plate inoculated with the NCI-H1299 cells from the incubator.
12. Use an 8-channel pipette to add 50 μl of the solution of each well of each column of the Round plate, starting from the dilute twelfth column, to the NCI-H1299 cells in the Flat Plate.
13. Incubate at 37° C. under 5% $CO_2$ for 120 h (5 days).
14. Count the wells in which 50% CPE is seen. Calculate the titer using the following formula.

$$\text{Log } 10(TCID_{50})=L+d(S-0.5)+\log 10(1/v)$$

<Cell Viability Measurement>
(Materials & Reagents)
96 well plate (flat bottom)
NCI-H1299, BEAS-2B, Het-1A cells ($1×10^4$ cells/80 μl/well)
RPMI 1640 w/10% FBS (growth medium)
Opti-MEM (registered trademark) I
CellTiter 96 (registered trademark) Aqueous One Solution Cell
Proliferation Assay
(Methods)
1. Inoculate the NCI-H1299, BEAS-2B, and Het-1A cells into the 96 well Flat plate at $1×10^4$ cells/80 μl/well.
2. Incubate at 37° C. under 5% $CO_2$ for 7 h.
3. Dilute the viruses with Opti-MEM to MOI=0.1 or MOI=1.
4. Place 20 μl of the diluted virus solutions in each well.
5. After 24, 48, and 72 hours, place 20 μl of the CellTiter 96 Reagent in each well, incubate for 1 hour, and measure the absorbance at 490 nm with Enspire.

<Tumorigenesis Test (In Vivo)>
(Materials & Reagents)
Mice: BALB/c nu-nu, 5-weeks-old, female, N=4/group
Viruses: CVB3-WT, CVB3-34aT-3, and CVB3-34cT-3
Tumor: NCI-H1299 ($5×10^6$ cells/100 μl PBS)
Control: Opti-MEM (registered trademark)
(Methods)
1. Day 0: Administer 0.1 ml/10 g (body weight) of a triple anesthetic combination (medetomidine hydrochloride 0.3 g+midazolam 4 mg+butorphanol tartrate 5 mg/kg anesthetic combination) into the abdominal cavity of each mouse with a 26 G needle. Subcutaneously administer $5×10^6$ cells/100 μl PBS/mouse of cancer cells of the cancer cell line (H1299) to the right abdominal region or left abdominal region of each mouse with a 27 G needle.
2. Day 2: Observe every other day and when the long diameter of a tumor of a mouse of the untreated group reaches 0.4 cm, disinfect the administration site with ethanol and thereupon administer 50 μl Opti-MEM/mouse into the tumor with a 29 G needle (alternate day administration; maximum of five times: day 2, 4, 6, 8, and 10).
3. Day 2: When the long diameter of a tumor of a mouse of a treated group reaches 0.4 cm, disinfect the administration site with ethanol and thereupon administer CVB3-WT or gene-modified CVB3 (CVB3-34aT-3 or CVB3-34cT-3) at $5×10^6$ $TCID_{50}$/50 μl Opti-MEM/mouse into the tumor with a 29 G needle inside a safety cabinet (alternate day administration; maximum of five times: day 2, 4, 6, 8, and 10).
4. Measure the body weight and the tumor diameter every other day, and euthanize immediately when the tumor long diameter exceeds 10 mm or the tumor becomes an ulcer (tumor volume=long diameter×short diameter×short diameter/2).
5. Even with a mouse for which a tumor does not form even after the elapse of three weeks or a tumor is completely rejected, set an observation period of up to 150 days maximum and then euthanize immediately.

<Blood Biochemical Examination (In Vivo)>
(Materials & Reagents)
Mice: BALB/c nu-nu, 5-weeks-old, female, N=4/group
Viruses: CVB3-WT, CVB3-34a&217T-53, and miR-1&2171
Tumor: NCI-H1299 ($5×10^6$ cells/100 μl PBS)
Control: Opti-MEM (registered trademark)
(Methods)
1. Day 0: Administer 0.1 ml/10 g (body weight) of a triple anesthetic combination (medetomidine hydrochloride 0.3 g+midazolam 4 mg+butorphanol tartrate 5 mg/kg anesthetic combination) into the abdominal cavity of each mouse with a 26 G needle. Subcutaneously administer $5×10^6$ cells/100 μl PBS/mouse of cancer cells of the cancer cell line (H1299) to the right abdominal region or left abdominal region of each mouse with a 27 G needle.
2. Day 2: Observe every other day and when the long diameter of a tumor of a mouse of the untreated group reaches 0.4 cm, disinfect the administration site with ethanol and thereupon administer 50 μl Opti-MEM/mouse into the tumor with a 29 G needle.
3. Day 2: When the long diameter of a tumor of a mouse of a treated group reaches 0.4 cm, disinfect the administration site with ethanol and thereupon administer CVB3-WT or gene-modified CVB3 (CVB3-34a&217T-53 or miR-1&217T) at $5×10^6$ $TCID_{50}$/50 μl Opti-MEM/mouse into the tumor with a 29 G needle inside a safety cabinet.

4. (For the one-dose group) Day 4: Administer 0.1 ml/10 g (body weight) of the triple anesthetic combination into the abdominal cavity of each mouse with a 26 G needle. Dissect the mouse and collect blood from the inferior vena cava with a 24 G needle (approx. 600 mL).
5. (For the two-dose group,) administer Opti-MEM or the virus into the tumor of each mouse one more time with a 29 G needle on day 4. Collect blood on day 6.
6. Leave the blood at room temperature for one hour (to coagulate) and then centrifuge at 1,500×g at room temperature for 15 minutes.
7. Transfer the supernatant (serum) into a new 1.5 mL tube.
8. Perform blood biochemical examination with Spot-Chem (registered trademark).

Sequence Listing Free Text
SEQ ID NO:1: miR-34a
SEQ ID NO:2: miR-34c
SEQ ID NO:3: miR-34aT×4+
SEQ ID NO:4: miR-34cT×4+
SEQ ID NO:5: miR-34aT×2 & miR-217T×2+
SEQ ID NO:6: miR-34cT×2 & miR-217T×2+
SEQ ID NO:7: miR-34aT×2 & miR-1T×2+
SEQ ID NO:8: miR-34cT×2 & miR-1T×2+
SEQ ID NO:9: miR-34a-Inverse Forward
SEQ ID NO:10: miR-34a-Inverse Reverse
SEQ ID NO:11: miR-34aT×4−
SEQ ID NO:12: miR-34c-Inverse Forward
SEQ ID NO:13: miR-34c-Inverse Reverse
SEQ ID NO:14: miR-34cT×4−
SEQ ID NO:15: CVB3-34a-5-Reverse
SEQ ID NO:16: CVB3-34a-5-Forward
SEQ ID NO:17: CVB3-34c-5-Reverse
SEQ ID NO:18: CVB3-34c-5-Forward
SEQ ID NO:19: CVB3-in-34c-5+
SEQ ID NO:20: CVB3-in-34c-5−
SEQ ID NO:21: CVB3-34a&217-5-Reverse
SEQ ID NO:22: CVB3-34a&217-5-Forward
SEQ ID NO:23: CVB3-34a&217-3-Reverse
SEQ ID NO:24: CVB3-34a&217-3-Forward
SEQ ID NO:25: miR-34a×2 & miR-217×2+
SEQ ID NO:26: miR-34a×2 & miR-217×2−
SEQ ID NO:27: CVB3-miR-Forward
SEQ ID NO:28: CVB3-miR-Reverse
SEQ ID NO:29: miR-1&217T Forward
SEQ ID NO:30: miR-1&217T Reverse

The invention claimed is:

1. A gene-modified coxsackievirus comprising:
a mutated genome including a coxsackievirus wild-type (CVB3-WT) genome, the CVB3-WT genome inserted with at least one polynucleotide wherein the polynucleotide includes a target sequence for a normal-cell-specific microRNA (miRNA),
wherein proliferation of the gene-modified coxsackievirus is suppressed specifically in normal cells and
wherein the target sequence for the normal-cell-specific miRNA corresponds to at least one of miR-34a and miR-34c, and
a position of insertion of the polynucleotide includes at least a position between position 742 and position 743 inside a 5' UTR region of the CVB3-WT genome,
wherein the position of insertion of the polynucleotide corresponds to being immediately upstream a base sequence comprising an initiation codon that initiates the translation of the CVB3-WT genome into proteins.

2. The gene-modified coxsackievirus according to claim 1, wherein the target sequence for the normal-cell-specific miRNA corresponds to miR-34a, and wherein positions of insertion of the polynucleotide are at least the position between the position 742 and the position 743 inside the 5' UTR region of the CVB3-WT genome and a position between position 7304 and position 7305 inside a 3' UTR region of the CVB3-WT genome.

3. The gene-modified coxsackievirus according to claim 2, wherein the polynucleotide has a sequence set forth by SEQ ID NO: 3.

4. The gene-modified coxsackievirus according to claim 2, wherein the polynucleotide further comprises a sequence set forth by SEQ ID NO: 5.

5. The gene-modified coxsackievirus according to claim 1, wherein a plurality of the polynucleotides are inserted.

6. The gene-modified coxsackievirus according to claim 1, wherein the gene-modified coxsackie virus capable of proliferating in cancer cells.

7. The gene-modified coxsackievirus according to claim 1, wherein the polynucleotide has a sequence set forth by SEQ ID NO: 3 or SEQ ID NO: 4.

8. The gene-modified coxsackievirus according to claim 1, wherein the polynucleotide is inserted inside each of the 5' UTR region and the 3' UTR region of the CVB3-WT genome.

9. The gene-modified coxsackievirus according to claim 1, wherein the mutated genome further comprises the CVB3-WT genome inserted with at least one polynucleotide including the target sequence for a tissue-specific microRNA (miRNA), wherein the tissue-specific miRNA further comprises at least one of miR-1 and miR-217 and a position of insertion of the polynucleotide including the target sequence for the tissue-specific miRNA includes at least a position between position 742 and position 743 inside a 5' UTR of CVB3-WT and a position between position 7304 and position 7305 inside the genome 3'UTR of CVB3-WT.

10. The gene-modified coxsackievirus according to claim 9, wherein the polynucleotide further comprises a sequence set forth by SEQ ID NO: 5 or SEQ ID NO: 6.

11. The gene-modified coxsackievirus according to claim 10, wherein the polynucleotide is inserted inside each of the 5' UTR region and the 3' UTR region of the CVB3-WT genome.

12. The gene-modified coxsackievirus according to claim 9, wherein the polynucleotide further comprises a sequence set forth by SEQ ID NO: 7 or SEQ ID NO: 8.

13. A pharmaceutical composition including the gene-modified coxsackievirus according to claim 1.

* * * * *

SEQUENCE LISTING

```
<160> NUMBER OF SEQ ID NOS: 30

<210> SEQ ID NO 1
<211> LENGTH: 22
<212> TYPE: RNA
<213> ORGANISM: Coxsackievirus

<400> SEQUENCE: 1
uggcaguguc uuagcugguu gu                                              22

<210> SEQ ID NO 2
<211> LENGTH: 23
<212> TYPE: RNA
<213> ORGANISM: Coxsackievirus

<400> SEQUENCE: 2
aggcagugua guuagcugau ugc                                             23

<210> SEQ ID NO 3
<211> LENGTH: 102
<212> TYPE: DNA
<213> ORGANISM: Coxsackievirus

<400> SEQUENCE: 3
acaaccagct aagacactgc cacgatacaa ccagctaaga cactgccaac cggtacaacc     60
agctaagaca ctgccatcac acaaccagct aagacactgc ca                       102

<210> SEQ ID NO 4
<211> LENGTH: 106
<212> TYPE: DNA
<213> ORGANISM: Coxsackievirus

<400> SEQUENCE: 4
gcaatcagct aactacactg cctcgatgca atcagctaac tacactgcct accggtgcaa     60
tcagctaact acactgcctt cacgcaatca gctaactaca ctgcct                   106

<210> SEQ ID NO 5
```

```
<211> LENGTH: 104
<212> TYPE: DNA
<213> ORGANISM: Coxsackievirus

<400> SEQUENCE: 5
acaaccagct aagacactgc cacgatacaa ccagctaaga cactgccaac cggttccaat      60
cagttcctga tgcagtatca ctccaatcag ttcctgatgc agta                      104

<210> SEQ ID NO 6
<211> LENGTH: 106
<212> TYPE: DNA
<213> ORGANISM: Coxsackievirus

<400> SEQUENCE: 6
gcaatcagct aactacactg cctcgatgca atcagctaac tacactgcct accggttcca      60
atcagttcct gatgcagtat cactccaatc agttcctgat gcagta                    106

<210> SEQ ID NO 7
<211> LENGTH: 102
<212> TYPE: DNA
<213> ORGANISM: Coxsackievirus

<400> SEQUENCE: 7
acaaccagct aagacactgc cacgatacaa ccagctaaga cactgccaac cggtatacat      60
acttctttac attccatcac atacatactt ctttacattc ca                        102

<210> SEQ ID NO 8
<211> LENGTH: 104
<212> TYPE: DNA
<213> ORGANISM: Coxsackievirus

<400> SEQUENCE: 8
gcaatcagct aactacactg cctcgatgca atcagctaac tacactgcct accggtatac      60
atacttcttt acattccatc acatacatac ttctttacat tcca                      104

<210> SEQ ID NO 9
<211> LENGTH: 47
<212> TYPE: DNA
<213> ORGANISM: Coxsackievirus

<400> SEQUENCE: 9
aaccagctaa gacactgcca gagacaattt gaaataattt agattgg                    47

<210> SEQ ID NO 10
<211> LENGTH: 41
<212> TYPE: DNA
<213> ORGANISM: Coxsackievirus

<400> SEQUENCE: 10
gcagtgtctt agctggttgt taatctaaaa ggagtccaac c                          41

<210> SEQ ID NO 11
<211> LENGTH: 102
<212> TYPE: DNA
<213> ORGANISM: Coxsackievirus

<400> SEQUENCE: 11
tggcagtgtc ttagctggtt gtgtgatggc agtgtcttag ctggttgtac cggttggcag      60
tgtcttagct ggttgtatcg tggcagtgtc ttagctggtt gt                        102
```

<210> SEQ ID NO 12
<211> LENGTH: 47
<212> TYPE: DNA
<213> ORGANISM: Coxsackievirus

<400> SEQUENCE: 12
atcagctaac tacactgcct gagacaattt gaaataattt agattgg         47

<210> SEQ ID NO 13
<211> LENGTH: 41
<212> TYPE: DNA
<213> ORGANISM: Coxsackievirus

<400> SEQUENCE: 13
cagtgtagtt agctgattgc taatctaaaa ggagtccaac c               41

<210> SEQ ID NO 14
<211> LENGTH: 106
<212> TYPE: DNA
<213> ORGANISM: Coxsackievirus

<400> SEQUENCE: 14
aggcagtgta gttagctgat tgcgtgaagg cagtgtagtt agctgattgc accggtaggc    60
agtgtagtta gctgattgca tcgaggcagt gtagttagct gattgc                  106

<210> SEQ ID NO 15
<211> LENGTH: 44
<212> TYPE: DNA
<213> ORGANISM: Coxsackievirus

<400> SEQUENCE: 15
gcagtgtctt agctggttgt tttgctgtat tcaacttaac aatg           44

<210> SEQ ID NO 16
<211> LENGTH: 40
<212> TYPE: DNA
<213> ORGANISM: Coxsackievirus

<400> SEQUENCE: 16
aaccagctaa gacactgcca atgggagctc aagtatcaac                40

<210> SEQ ID NO 17
<211> LENGTH: 31
<212> TYPE: DNA
<213> ORGANISM: Coxsackievirus

<400> SEQUENCE: 17
gctttgctgt attcaactta acaatgaatt g                          31

<210> SEQ ID NO 18
<211> LENGTH: 20
<212> TYPE: DNA
<213> ORGANISM: Coxsackievirus

<400> SEQUENCE: 18
atgggagctc aagtatcaac                                      20

<210> SEQ ID NO 19
<211> LENGTH: 136
<212> TYPE: DNA
<213> ORGANISM: Coxsackievirus

<400> SEQUENCE: 19

```
gttgaataca gcaaagcaat cagctaacta cactgcctcg atgcaatcag ctaactacac        60
tgcctaccgg tgcaatcagc taactacact gccttcacgc aatcagctaa ctacactgcc       120
tatgggagct caagta                                                       136

<210> SEQ ID NO 20
<211> LENGTH: 136
<212> TYPE: DNA
<213> ORGANISM: Coxsackievirus

<400> SEQUENCE: 20
tacttgagct cccataggca gtgtagttag ctgattgcgt gaaggcagtg tagttagctg        60
attgcaccgg taggcagtgt agttagctga ttgcatcgag gcagtgtagt tagctgattg       120
ctttgctgta ttcaac                                                       136

<210> SEQ ID NO 21
<211> LENGTH: 44
<212> TYPE: DNA
<213> ORGANISM: Coxsackievirus

<400> SEQUENCE: 21
gcagtgtctt agctggttgt tttgctgtat tcaacttaac aatg                         44

<210> SEQ ID NO 22
<211> LENGTH: 42
<212> TYPE: DNA
<213> ORGANISM: Coxsackievirus

<400> SEQUENCE: 22
aatcagttcc tgatgcagta atgggagctc aagtatcaac gc                           42

<210> SEQ ID NO 23
<211> LENGTH: 46
<212> TYPE: DNA
<213> ORGANISM: Coxsackievirus

<400> SEQUENCE: 23
gcagtgtctt agctggttgt taatctaaaa ggagtccaac cacttc                       46

<210> SEQ ID NO 24
<211> LENGTH: 46
<212> TYPE: DNA
<213> ORGANISM: Coxsackievirus

<400> SEQUENCE: 24
aatcagttcc tgatgcagta gagacaattt gaaataattt agattg                       46

<210> SEQ ID NO 25
<211> LENGTH: 104
<212> TYPE: DNA
<213> ORGANISM: Coxsackievirus

<400> SEQUENCE: 25
acaaccagct aagacactgc cacgatacaa ccagctaaga cactgccaac cggttccaat        60
cagttcctga tgcagtatca ctccaatcag ttcctgatgc agta                        104

<210> SEQ ID NO 26
<211> LENGTH: 104
<212> TYPE: DNA
<213> ORGANISM: Coxsackievirus

<400> SEQUENCE: 26
```

```
tactgcatca ggaactgatt ggagtgatac tgcatcagga actgattgga accggttggc    60
agtgtcttag ctggttgtat cgtggcagtg tcttagctgg ttgt                    104

<210> SEQ ID NO 27
<211> LENGTH: 20
<212> TYPE: DNA
<213> ORGANISM: Coxsackievirus

<400> SEQUENCE: 27
caggtctttg aggggaacaa                                                20

<210> SEQ ID NO 28
<211> LENGTH: 20
<212> TYPE: DNA
<213> ORGANISM: Coxsackievirus

<400> SEQUENCE: 28
attaatgcag ctggcacgac                                                20

<210> SEQ ID NO 29
<211> LENGTH: 129
<212> TYPE: DNA
<213> ORGANISM: Coxsackievirus

<400> SEQUENCE: 29
ttaatacata cttctttaca ttccacgata tacatacttc tttacattcc aaccggttcc    60
aatcagttcc tgatgcagta tcactccaat cagttcctga tgcagtagag acaatttgaa   120
ataatttag                                                           129

<210> SEQ ID NO 30
<211> LENGTH: 129
<212> TYPE: DNA
<213> ORGANISM: Coxsackievirus

<400> SEQUENCE: 30
ctctactgca tcaggaactg attggagtga tactgcatca ggaactgatt ggaaccggtt    60
ggaatgtaaa gaagtatgta tatcgtggaa tgtaaagaag tatgtattaa tctaaaagga   120
gtccaacca                                                           129
```